(12) United States Patent　　　(10) Patent No.:　　US 7,267,959 B2
Gaisano　　　　　　　　　　　　　(45) Date of Patent:　　Sep. 11, 2007

(54) DRUG TARGET WITHIN THE SULFONYLUREA RECEPTOR

(76) Inventor: Herbert Young Gaisano, 281 Elmwood Avenue, Willowdale, Ontario (CA) M2N 3M9

( * ) Notice: Subject to any disclaimer, the term of this patent is extended or adjusted under 35 U.S.C. 154(b) by 599 days.

(21) Appl. No.: 10/466,313

(22) PCT Filed: Jan. 30, 2002

(86) PCT No.: PCT/CA02/00108

§ 371 (c)(1),
(2), (4) Date: Jul. 28, 2003

(87) PCT Pub. No.: WO02/061431

PCT Pub. Date: Aug. 8, 2002

(65) Prior Publication Data

US 2004/0102359 A1　　May 27, 2004

Related U.S. Application Data

(60) Provisional application No. 60/264,690, filed on Jan. 30, 2001.

(51) Int. Cl.
*G01N 33/53*　　　(2006.01)
*C07K 1/00*　　　　(2006.01)
*C07K 14/47*　　　(2006.01)

(52) U.S. Cl. .................. 435/7.1; 530/350; 530/810
(58) Field of Classification Search .................. None
See application file for complete search history.

(56) References Cited

OTHER PUBLICATIONS

Cui et al., H3 domain of syntaxin-1A inhibits Kalp channels by its actions onthe sulfonylurea receptor 1 nucleotide binding folds -1 and -2, 2004, vol. 279, Issue 51, pp. 53259-53265.*
Moreau et al., SUR., ABC proteins targeted by KATP channel openers, 2005, vol. 38, pp. 951-963.*
Hough et al., Expression, purification, and evidence for the interaction of two nucleotide-binding folds of the sulphonylurea receptor, 2002, Biochemical and Biophysical Research Communications, vol. 294, pp. 191-197.*
Janson, L. et al., "$K_{ATP}$ Channels and Pancreatic Islet Blood Flow in Anesthetized Rats", Diabetes, 2003, pp. 2043-2048, vol. 52.
Seino, S., "ATP-Sensitive Potassium Channels: A Model of Heteromultimeric Potassium Channel/Receptor Assemblies", Annu. Rev. Physiol., 1999, pp. 337-362, vol. 61.
Chutkow, W.A. et al., "Cloning, Tissue Expression, and Chromosomal Localization of SUR2, the Putative Drug-Binding Subunit of Cardiac, Skeletal Muscle, and Vascular $K_{ATP}$ Channels", Diabetes, 1996, pp. 1439-1445, vol. 45.
Lawson, K., "Potassium channel openers as potential therapeutic weapons in ion channel disease", Kidney International, 2000, pp. 838-845, vol. 57.
Tucker, S.J. et al., "Molecular determinants of $K_{ATP}$ channel inhibition by ATP", The EMBO Journal, 1998, pp. 3290-3296, vol. 17, No. 12.
Gribble, F. M. et al., The essential role of the Walker A motifs of SUR1 in K-ATP channel activation by Mg-ADP and diazoxide, The EMBO Journal, 1997, pp. 1145-1152, vol. 16, No. 8.
Shyng, S-L et al., "Regulation of $K_{ATP}$ Channel Activity by Diazoxide and MgADP: Distinct Functions of the Two Nucleotide Binding Folds of the Sulfonylurea Receptor", J. Gen. Physiol, 1997, pp. 643-654, vol. 110.
Nichols, C.G. et al., "Adenosine diphosphate as an intracellular regulator of insulin secretion", Science, 1996, pp. 1785-1787, vol. 272.
Ueda, K. et al., "MgADP Antagonism to $Mg^{2+}$ Independent ATP Binding of the Sulfonylurea Receptor SUR1", The Journal of Biological Chemistry, 1997, pp. 22983-22986, vol. 272, No. 37.
Schwanstecher, M. et al., "Potassium channel openers require ATP to bind to and act through sulfonylurea receptors", The EMBO Journal, 1998, pp. 5529-5535, vol. 17, No. 19.
Misura, K.M.S. et al., "Three-dimensional structure of the neuronal-Sec1-syntaxin 1a complex", Nature, 2000, pp. 355-362, vol. 404.
Fasshauer, D. et al,, "Conserved Structural Features of the Synaptic Fusion Complex: SNARE Proteins Reclassified as Q-and R-SNAREs" Proceedings of the National Academy of Sciences Untied States of America, 1998, pp. 15781-15786, vol. 95, No. 26.
Naren, A.P. et al., "Regulation of CFTR chloride channels by syntaxin and Munc18 isoforms", Nature, 1997, pp. 302-305, vol. 390.
Naren, A.P. et al., "Syntaxin 1A Inhibits CFTR Chloride Channels by means of Domain-Specific Protein—Protein Interactions", Proceedings of the National Academy of Sciences of the United States of America, 1998, pp. 10972-10977, vol. 95, No. 18.
de Tullio, P. et al., "Toward Tissue-Selective Pancreatic B-Cells $K_{ATP}$ Channel Openers Belonging to 3-Alkylamino-7-halo-4H-,2,4-benzothiadiazine 1,1-Dioxides", J. Med. Chem., 2003, pp. 3342-3353, vol. 46.

(Continued)

*Primary Examiner*—Bridget Bunner
*Assistant Examiner*—Ian Dang
(74) *Attorney, Agent, or Firm*—Bereskin & Parr; Micheline Gravelle

(57) ABSTRACT

It has been found that syntaxin binds and regulates the nucleotide binding folds (NBFs) of sulfonylurea receptors (SURs) in a ATP- and ADP-dependent manner. The present invention therefore provides methods for identifying compounds that effect the binding between a syntaxin protein and a NBF1 and/or NBF2 of a sulfonylurea receptor (SUR). Compounds identified using the method of the invention are useful for treating and/or preventing diseases and/or conditions that have, as their underlying basis, a dysregulation of $K_{AT}$191 channels.

9 Claims, 9 Drawing Sheets

OTHER PUBLICATIONS

Carr, R.D. et al., "NN414, a SUR1/Kir6.2-Selective Potassium Channel Opener, Reduces Blood Glucose and Improves Glucose Tolerance in the VDF Zucker Rat", Diabetes, 2003, pp. 2513-2518, vol. 52, No. 10.

Pasyk, E.A. et al., "Syntaxin-1A Binds the Nucleotide-binding Folds of Suphyonylurea Receptor 1 to Regulate the $K_{ATP}$ Channel", 2004, pp. 4234-4240, vol. 279, No. 6.

Higgins, C., "The ABC of Channel Regulation", Cell, 1995, pp. 693-696, vol. 82.

Sutton, R.B. et al., "Crystal structure of SNARE complex involved in synaptic exocytosis at 2.4 Å resolution", Nature, 1998, pp. 347-353, vol. 395.

* cited by examiner

FIGURE 2

MKDRTQELRTAKDSDDDDDVTVTVDRDRFMDEFFEQVEEIRGFIDKIAEN
VEEVKRKHSAILASPNPDEKTKEELEELMSDIKKTANKVRSKLKSIEQSI
EQEEGLNRSSADLRIRKTQHSTLSRKFVEVMSEYNATQSDYRERCKGRIQ
RQLEITGRTTTSEELEDMLESGNPAIFASGIIMDSSISKQ<u>ALSEIETRHS</u>
<u>EIIKLENRLRELHDMFMDMAMLVESQGEMIDRIEYNVEHAVDYVERAVSD</u>
<u>TKKAVKYQSKARRKKI</u>MIIICCVILGIIACTIGGIFG

FIGURE 3A

NBF-1

```
                                    SUR-1   LSNITIRIPRGQLTMIVGQVGC
                                    SUR-2A  LSNIDIRIPTGQLTMIVGQVGC
                                    ****  ****  ************
GKSSLLLATLGEMQKVSGAVFWNSNLPDSEGEDPSSPERETAAGSDIRSRGPVAYASQKP
GKSSLLLAILGEMQTLEGKVYWN-NVNESE---PSF-EATRS-----RSRYSVAYAAQKP
********  *****    *  *  ** *   **   **   *        ***  ****  ***
WLLNATVEENITFESPFNKQRYKMVIEACSLQPDIDILPHGDQTQIGERGINLSGGQRQR
WLLNATVEENITFGSPFNRQRYKAVTDACSLQPDIDLLPFGDQTEIGERGINLSGGQRQK
*************  ****  ****  *   *********  **  ****  *************
ISVARALYQQTNVVFLDDPFSALDVHLSDHLMQAGILELLRDDKRTVVLVTHKLQYL
ICVARALYQNTNIVFLDDPFSALDIHLSDHLMQEGILKFLQDDKRTVVLVTHKLQYL
*  *******  **  ***********  *******  ***    *  ****************
```

NBF-2

```
                                    SUR-1   LKPVLKHVNTLISPGQKIG
                                    SUR-2A  LKPVLKHVKAYIKPGQKVG
                                    ********     *  **** *
ICGRTGSGKSSFSLAFFRMVDMFEGRIIIDGIDIAKLPLHTLRSRLSIILQDPVLFSGTI
ICGRTGSGKSSLSLAFFRMVDIFDGKIVIDGIDISKLPLHTLRSRLSIILQDPILFSGSI
***********  *********   *  *  *   ******   ********************  ****  *
RFNLDPEKKCSDSTLWEALEIAQLKLVVKALPGGLDAIITEGGENFSQGQRQLFCLARAF
RFNLDPECKCTDDRLWEALEIAQLKNMVKSLPGGLDATVTEGGENFSVGQRQLFCLARAF
*******  **  *   **********   **  *******    *******   *************
VRKTSIFIMDEATASIDMATENILQKVVMTAFADRTVVTI
VRKSSILIMDEATASIDMATENILQKVVMTAFADRTVVTI
***  **  *******************************
```

FIGURE 3B

NBF-1

```
                    SUR-1   LSNITIRIPRGQLTMIVGQVGCGK
                    SUR-2B  LSNIDIRIPTGQLTMIVGQVGCGK
                            ****.****.*************
SSLLLATLGEMQKVSGAVFWNSNLPDSEGEDPSSPERETAAGSDIRSRGPVAYASQKPWL
SSLLLAILGEMQTLEGKVYWN-NVNESE------PSFEATRS---RSRYSVAYAAQKPWL
******.*****.*.**.*.**.          *.*.   *** ****.*****
LNATVEENITFESPFNKQRYKMVIEACSLQPDIDILPHGDQTQIGERGINLSGGQRQRIS
LNATVEENITFGSPFNRQRYKAVTDACSLQPDIDLLPFGDQTEIGERGINLSGGQRQKIC
***********.****.****.*.********.**.****.************* *
VARALYQQTNVVFLDDPFSALDVHLSDHLMQAGILELLRDDKRTVVLV
VARALYQNTNIVFLDDPFSALDIHLSDHLMQEGILKFLQDDKRTVVLV
*******.**.**********.********.***..*.*********
```

NBF-2

```
                    SUR-1   LKPVLKHVNTLISPGQKIGICG
                    SUR-2B  LKPVLKHVKAYIKPGQKVGICG
                            ********. . .*.****.****
RTGSGKSSFSLAFFRMVDMFEGRIIIDGIDIAKLPLHTLRSRLSIILQDPVLFSGTIRFN
RTGSGKSSLSLAFFRMVDIFDGKIVIDGIDISKLPLHTLRSRLSIILQDPILFSGSIRFN
********.*********.*.*.*.******.*****************.****.****
LDPEKKCSDSTLWEALEIAQLKLVVKALPGGLDAIITEGGENFSQGQRQLFCLARAFVRK
LDPECKCTDDRLWEALEIAQLKNMVKSLPGGLDATVTEGGENFSVGQRQLFCLARAFVRK
****.**.*.*.**********. .**.********..*******.**************
TSIFIMDEATASIDMATENILQKVVMTAFADRTVVTI
SSILIMDEATASIDMATENILQKVVMTAFADRTVVTI
.*.*********************************
```

FIGURE 3C

NBF-1

SUR-2A LSNIDIRIPTGQLTMIVGQVGCGKSSLL
SUR-2B LSNIDIRIPTGQLTMIVGQVGCGKSSLL
        ****************************

LAILGEMQTLEGKVYWNNVNESEPSFEATRSRSRYSVAYAAQKPWLLNATVEENITFGSP
LAILGEMQTLEGKVYWNNVNESEPSFEATRSRSRYSVAYAAQKPWLLNATVEENITFGSP
************************************************************
FNRQRYKAVTDACSLQPDIDLLPFGDQTEIGERGINLSGGQRQKICVARALYQNTNIVFL
FNRQRYKAVTDACSLQPDIDLLPFGDQTEIGERGINLSGGQRQKICVARALYQNTNIVFL
************************************************************
DDPFSALDIHLSDHLMQEGILKFLQDDKRTVVLVTHKLQYL
DDPFSALDIHLSDHLMQEGILKFLQDDKRTVVLVTHKLQYL
****************************************

NBF-2

SUR-2A LKPVLKHVKAYIKPGQKVGICGRTGSGKSSLSLAFFRMVDIFDGKIVIDGI
SUR-2B LKPVLKHVKAYIKPGQKVGICGRTGSGKSSLSLAFFRMVDIFDGKIVIDGI
       **************************************************
DISKLPLHTLRSRLSIILQDPILFSGSIRFNLDPECKCTDDRLWEALEIAQLKNMVKSLP
DISKLPLHTLRSRLSIILQDPILFSGSIRFNLDPECKCTDDRLWEALEIAQLKNMVKSLP
***********************************************************
GGLDATVTEGGENFSVGQRQLFCLARAFVRKSSILIMDEATASIDMATENILQKVVMTAF
GGLDATVTEGGENFSVGQRQLFCLARAFVRKSSILIMDEATASIDMATENILQKVVMTAF
***********************************************************
ADRTVVTI
ADRTVVTI
********

FIGURE 5
A
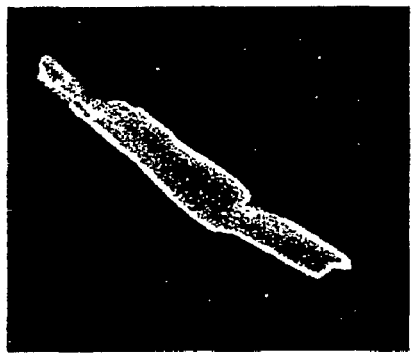
B
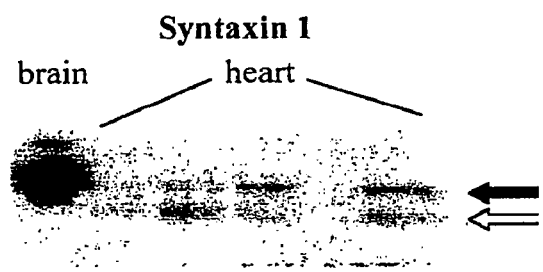

SEQUENCE LISTING

<160> NUMBER OF SEQ ID NOS: 7

<210> SEQ ID NO 1
<211> LENGTH: 288
<212> TYPE: PRT
<213> ORGANISM: Rattus norvegicus

<400> SEQUENCE: 1

```
Met Lys Asp Arg Thr Gln Glu Leu Arg Thr Ala Lys Asp Ser Asp Asp
1               5                   10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95
```

```
Glu Gln Ser Ile Glu Gln Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Arg
        195                 200                 205

Leu Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Ile Ile Ala Cys Thr Ile Gly Gly Ile Phe Gly
        275                 280                 285

<210> SEQ ID NO 2
<211> LENGTH: 199
<212> TYPE: PRT
<213> ORGANISM: Rattus norvegicus

<400> SEQUENCE: 2

Leu Ser Asn Ile Thr Ile Arg Ile Pro Arg Gly Gln Leu Thr Met Ile
1               5                   10                  15

Val Gly Gln Val Gly Cys Gly Lys Ser Ser Leu Leu Leu Ala Thr Leu
            20                  25                  30

Gly Glu Met Gln Lys Val Ser Gly Ala Val Phe Trp Asn Ser Asn Leu
        35                  40                  45

Pro Asp Ser Glu Gly Glu Asp Pro Ser Ser Pro Glu Arg Glu Thr Ala
    50                  55                  60

Ala Gly Ser Asp Ile Arg Ser Arg Gly Pro Val Ala Tyr Ala Ser Gln
65                  70                  75                  80

Lys Pro Trp Leu Leu Asn Ala Thr Val Glu Glu Asn Ile Thr Phe Glu
                85                  90                  95

Ser Pro Phe Asn Lys Gln Arg Tyr Lys Met Val Ile Glu Ala Cys Ser
            100                 105                 110

Leu Gln Pro Asp Ile Asp Ile Leu Pro His Gly Asp Gln Thr Gln Ile
        115                 120                 125

Gly Glu Arg Gly Ile Asn Leu Ser Gly Gly Gln Arg Gln Arg Ile Ser
    130                 135                 140

Val Ala Arg Ala Leu Tyr Gln Gln Thr Asn Val Val Phe Leu Asp Asp
145                 150                 155                 160

Pro Phe Ser Ala Leu Asp Val His Leu Ser Asp His Leu Met Gln Ala
                165                 170                 175
```

```
Gly Ile Leu Glu Leu Leu Arg Asp Asp Lys Arg Thr Val Val Leu Val
            180                 185                 190

Thr His Lys Leu Gln Tyr Leu
        195
```

<210> SEQ ID NO 3
<211> LENGTH: 179
<212> TYPE: PRT
<213> ORGANISM: Rattus norvegicus

<400> SEQUENCE: 3

```
Leu Lys Pro Val Leu Lys His Val Asn Thr Leu Ile Ser Pro Gly Gln
1               5                   10                  15

Lys Ile Gly Ile Cys Gly Arg Thr Gly Ser Gly Lys Ser Ser Phe Ser
            20                  25                  30

Leu Ala Phe Phe Arg Met Val Asp Met Phe Glu Gly Arg Ile Ile Ile
        35                  40                  45

Asp Gly Ile Asp Ile Ala Lys Leu Pro Leu His Thr Leu Arg Ser Arg
    50                  55                  60

Leu Ser Ile Ile Leu Gln Asp Pro Val Leu Phe Ser Gly Thr Ile Arg
65                  70                  75                  80

Phe Asn Leu Asp Pro Glu Lys Lys Cys Ser Asp Ser Thr Leu Trp Glu
                85                  90                  95

Ala Leu Glu Ile Ala Gln Leu Lys Leu Val Val Lys Ala Leu Pro Gly
            100                 105                 110

Gly Leu Asp Ala Ile Ile Thr Glu Gly Gly Glu Asn Phe Ser Gln Gly
        115                 120                 125

Gln Arg Gln Leu Phe Cys Leu Ala Arg Ala Phe Val Arg Lys Thr Ser
    130                 135                 140

Ile Phe Ile Met Asp Glu Ala Thr Ala Ser Ile Asp Met Ala Thr Glu
145                 150                 155                 160

Asn Ile Leu Gln Lys Val Val Met Thr Ala Phe Ala Asp Arg Thr Val
                165                 170                 175

Val Thr Ile
```

<210> SEQ ID NO 4
<211> LENGTH: 189
<212> TYPE: PRT
<213> ORGANISM: Rattus norvegicus

<400> SEQUENCE: 4

```
Leu Ser Asn Ile Asp Ile Arg Ile Pro Thr Gly Gln Leu Thr Met Ile
1               5                   10                  15

Val Gly Gln Val Gly Cys Gly Lys Ser Ser Leu Leu Leu Ala Ile Leu
            20                  25                  30

Gly Glu Met Gln Thr Leu Glu Gly Lys Val Tyr Trp Asn Asn Val Asn
        35                  40                  45

Glu Ser Glu Pro Ser Phe Glu Ala Thr Arg Ser Arg Ser Arg Tyr Ser
    50                  55                  60

Val Ala Tyr Ala Ala Gln Lys Pro Trp Leu Leu Asn Ala Thr Val Glu
65                  70                  75                  80

Glu Asn Ile Thr Phe Gly Ser Pro Phe Asn Arg Gln Arg Tyr Lys Ala
                85                  90                  95

Val Thr Asp Ala Cys Ser Leu Gln Pro Asp Ile Asp Leu Leu Pro Phe
            100                 105                 110
```

```
Gly Asp Gln Thr Glu Ile Gly Glu Arg Gly Ile Asn Leu Ser Gly Gly
        115                 120                 125

Gln Arg Gln Lys Ile Cys Val Ala Arg Ala Leu Tyr Gln Asn Thr Asn
    130                 135                 140

Ile Val Phe Leu Asp Asp Pro Phe Ser Ala Leu Asp Ile His Leu Ser
145                 150                 155                 160

Asp His Leu Met Gln Glu Gly Ile Leu Lys Phe Leu Gln Asp Asp Lys
                165                 170                 175

Arg Thr Val Val Leu Val Thr His Lys Leu Gln Tyr Leu
            180                 185

<210> SEQ ID NO 5
<211> LENGTH: 179
<212> TYPE: PRT
<213> ORGANISM: Rattus norvegicus

<400> SEQUENCE: 5

Leu Lys Pro Val Leu Lys His Val Lys Ala Tyr Ile Lys Pro Gly Gln
1               5                   10                  15

Lys Val Gly Ile Cys Gly Arg Thr Gly Ser Gly Lys Ser Ser Leu Ser
            20                  25                  30

Leu Ala Phe Phe Arg Met Val Asp Ile Phe Asp Gly Lys Ile Val Ile
        35                  40                  45

Asp Gly Ile Asp Ile Ser Lys Leu Pro Leu His Thr Leu Arg Ser Arg
    50                  55                  60

Leu Ser Ile Ile Leu Gln Asp Pro Ile Leu Phe Ser Gly Ser Ile Arg
65                  70                  75                  80

Phe Asn Leu Asp Pro Glu Cys Lys Cys Thr Asp Asp Arg Leu Trp Glu
                85                  90                  95

Ala Leu Glu Ile Ala Gln Leu Lys Asn Met Val Lys Ser Leu Pro Gly
            100                 105                 110

Gly Leu Asp Ala Thr Val Thr Glu Gly Gly Glu Asn Phe Ser Val Gly
        115                 120                 125

Gln Arg Gln Leu Phe Cys Leu Ala Arg Ala Phe Val Arg Lys Ser Ser
    130                 135                 140

Ile Leu Ile Met Asp Glu Ala Thr Ala Ser Ile Asp Met Ala Thr Glu
145                 150                 155                 160

Asn Ile Leu Gln Lys Val Val Met Thr Ala Phe Ala Asp Arg Thr Val
                165                 170                 175

Val Thr Ile

<210> SEQ ID NO 6
<211> LENGTH: 182
<212> TYPE: PRT
<213> ORGANISM: Rattus norvegicus

<400> SEQUENCE: 6

Leu Ser Asn Ile Asp Ile Arg Ile Pro Thr Gly Gln Leu Thr Met Ile
1               5                   10                  15

Val Gly Gln Val Gly Cys Gly Lys Ser Ser Leu Leu Leu Ala Ile Leu
            20                  25                  30

Gly Glu Met Gln Thr Leu Glu Gly Lys Val Tyr Trp Asn Asn Val Asn
        35                  40                  45

Glu Ser Glu Pro Ser Phe Glu Ala Thr Arg Ser Arg Ser Arg Tyr Ser
    50                  55                  60
```

-continued

```
Val Ala Tyr Ala Ala Gln Lys Pro Trp Leu Leu Asn Ala Thr Val Glu
 65                  70                  75                  80

Glu Asn Ile Thr Phe Gly Ser Pro Phe Asn Arg Gln Arg Tyr Lys Ala
                 85                  90                  95

Val Thr Asp Ala Cys Ser Leu Gln Pro Asp Ile Asp Leu Leu Pro Phe
            100                 105                 110

Gly Asp Gln Thr Glu Ile Gly Glu Arg Gly Ile Asn Leu Ser Gly Gly
        115                 120                 125

Gln Arg Gln Lys Ile Cys Val Ala Arg Ala Leu Tyr Gln Asn Thr Asn
    130                 135                 140

Ile Val Phe Leu Asp Asp Pro Phe Ser Ala Leu Asp Ile His Leu Ser
145                 150                 155                 160

Asp His Leu Met Gln Glu Gly Ile Leu Lys Phe Leu Gln Asp Asp Lys
                165                 170                 175

Arg Thr Val Val Leu Val
                180
```

<210> SEQ ID NO 7
<211> LENGTH: 179
<212> TYPE: PRT
<213> ORGANISM: Rattus norvegicus

<400> SEQUENCE: 7

```
Leu Lys Pro Val Leu Lys His Val Lys Ala Tyr Ile Lys Pro Gly Gln
  1               5                  10                  15

Lys Val Gly Ile Cys Gly Arg Thr Gly Ser Gly Lys Ser Ser Leu Ser
                 20                  25                  30

Leu Ala Phe Phe Arg Met Val Asp Ile Phe Asp Gly Lys Ile Val Ile
             35                  40                  45

Asp Gly Ile Asp Ile Ser Lys Leu Pro Leu His Thr Leu Arg Ser Arg
     50                  55                  60

Leu Ser Ile Ile Leu Gln Asp Pro Ile Leu Phe Ser Gly Ser Ile Arg
 65                  70                  75                  80

Phe Asn Leu Asp Pro Glu Cys Lys Cys Thr Asp Asp Arg Leu Trp Glu
                 85                  90                  95

Ala Leu Glu Ile Ala Gln Leu Lys Asn Met Val Lys Ser Leu Pro Gly
            100                 105                 110

Gly Leu Asp Ala Thr Val Thr Glu Gly Gly Glu Asn Phe Ser Val Gly
        115                 120                 125

Gln Arg Gln Leu Phe Cys Leu Ala Arg Ala Phe Val Arg Lys Ser Ser
    130                 135                 140

Ile Leu Ile Met Asp Glu Ala Thr Ala Ser Ile Asp Met Ala Thr Glu
145                 150                 155                 160

Asn Ile Leu Gln Lys Val Val Met Thr Ala Phe Ala Asp Arg Thr Val
                165                 170                 175

Val Thr Ile
```

DRUG TARGET WITHIN THE SULFONYLUREA RECEPTOR

RELATED APPLICATIONS

The present application is the national phase entry of PCT/CA02/00108, filed Jan. 30, 2002 which claims the benefit of priority under 35 U.S.C. 119(e) from U.S. provisional patent application number 60/264,690, foled Jan. 30, 2001.

FIELD OF THE INVENTION

The present invention relates assays for compounds that modulate potassium ($K_{ATP}$) channels in cells. In particular, the invention relates to methods of assaying for compounds that modulate the interaction between the sulfonylurea receptor and a binding protein.

BACKGROUND OF THE INVENTION

Electrically-excitable cells include not only neurons and neuroendocrine cells (i.e. pancreatic islet β-cells), but also cardiac and muscle cells. The electrical activity (membrane potential) of these excitable cells is regulated by membrane ion channels which effect either membrane depolarization or repolarization.

The $K_{ATP}$ channel has been best studied in the pancreatic islet β-cell[1,11,12] whereby glucose entry and metabolism into the islet β-cell generates a change in the ratio of adenine nucleotides, adenosine trisphosphate (ATP) and adenosine diphosphate (ADP). Increased ATP and decreased ADP cause a closure of the plasma membrane $K_{ATP}$ channel proteins. The resulting cell membrane depolarization then causes the opening of $Ca^{2+}$ channels which effects $Ca^{2+}$ influx into the cell to act on a set of SNARE proteins on the insulin secretory granules and plasma membrane which come together to form a complex that induces the fusion of the granule to the membrane and subsequent release of insulin.

In the normal cardiac muscle, the $K_{ATP}$ channels are closed by the high intracellular ATP concentrations [ATP].[2,13] However, during ischemia, the [ATP] are lowered, and results in the opening of $K_{ATP}$ channels, and the resulting increase in outward $K^+$ currents shortens the duration of membrane action potentials, leading to a reduction of $Ca^{2+}$ influx, and consequent reduced contraction and energy consumption. The $K_{ATP}$ channel opening therefore serves to protect the myocardium from ischemic injury.[2,13]

These $K_{ATP}$ channels are each composed of two distinct subunits, SUR and a member of the inward rectifying $K_{ATP}$ channel family, Kir6.X, which is the actual gating pore.[1] There are several isoforms of SUR.[1] SUR1A (1581 aa, 177 kDa) is the dominant isoform in pancreatic islets and brain,[3] SUR 2A[4,5] (1545 aa, 174 kD) in the heart and skeletal muscle, SUR2B[4,5,7] (1546 aa, 175 kD) in smooth muscle and vascular smooth muscle and the more ubiquitously expressed SUR2C (1512 aa, 170 kD).[5] Kir6.X[2,6-8] has two isoforms including Kir6.1 in smooth muscle and Kir6.2 in cardiac and skeletal muscles, pancreatic islets and brain. These SUR and Kir6.X proteins come together (i.e. SUR1A/Kir6.2, SUR2A/Kir6.2, SUR2B/Kir6.1) to form hetero-octamer (4SUR+4Kir6.X)[1,14] proteins in the native cell plasma membrane. Each of the SUR proteins contains two large (180-200 aa) cytoplasmic folds (NBF1 and NBF2) each of which contains Walker A ($W_A$) and Walker B ($W_B$) motifs (FIG. 1).[1] The Walker motifs form nucleotide binding pockets (hence called nucleotide binding fold-NBF). Much is known about the SUR1/Kir6.2 structure-function, as these were the first to be cloned,[3,6,8] and because of its presence in islet β-cells and consequent therapeutic relevance to diabetes. Genetic mutations for the disease familial persistent hyperinsulinemic hypoglycemia of infancy PHHI[15] were identified (G1479R in NBF2) within SUR1 to cause the pathologic closure of the $K_{ATP}$ channel. Discovery of such mutations further contributed to the elucidation of the structure-function of SUR1. However, no such mutations have been found with SUR2. In both SUR1 and SUR2, ATP closes the $K_{ATP}$ channel by binding to the SUR subunit, as well as Kir6.2.[1,6,17] Upon ATP hydrolysis to ADP, the ADP in combination with $Mg^{2+}$, opens the $K_{ATP}$ channel mainly by binding to NBF2.[8,20] Both NBFs act cooperatively to modulate not only MgADP binding and activity, but also Kir6.2 regulation by ATP.[1] In fact, early studies showed that ATP has a secondary, albeit non-essential, binding site at NBF1 which prolongs $K_{ATP}$ opening.[21]

Overall, there is a 68% homology between SUR1 and SUR2A at the amino acid level,[4] and the heterogeneity is attributed to the N-terminal transmembrane and the very C-terminal domains.[22] Of a total of 17 transmembrane segments, the N-terminal five transmembrane helical domain confers the distinct binding affinity to sulfonylureas (100× higher affinity to SUR1>SUR2A) and burst intervals (shorter for SUR1 than SUR2A).[4,22] In contrast, the NBF1 and NBF2 domains between the SUR1 and SUR2A possess very high homology.[4] At the amino acid level, SUR1-NBF1 (aa 694-893) and SUR2A-NBF1 (aa 682-873) has a 81.4% homology, whereas SUR1-NBF2 (aa 1356-1535) and SUR2A-NBF2 (1320-1499) has a 86.6% homology.[4] SUR2 has 3 alternatively spliced variants, SUR2A, SUR2B and SUR2C.[1] SUR2A and SUR2B differ only in the last 42 amino acids at the C-terminus which is just outside the NBF2 region.[4,22] Interestingly the C-terminal 42 aa domain of SUR2B is more similar to that in SUR1 (aa 1539-1581).[7] The distinct C-terminus (42 aa) of the SURs confers the different ATP sensitivity[22] (4-fold higher ATP sensitivity in SUR1 than SUR2A and SUR2B) and MgADP actions[23] (increases potassium channel opener (KCO) binding to SUR2A, inhibits KCO binding to SUR2B[24]). Compared to SUR2A, SUR2C has a 35 amino acid deletion just outside the N-terminal end of NBF1 which corresponds to aa 635-670 region of SUR2A,[5] and this region is interestingly also the most divergent region between SUR2A and SUR1.[4] The NBF1s and NBF2s are therefore very well conserved between the SUR1 and SUR2 isoforms.

There has not been a ternary protein found to bind and regulate SUR or Kir6.2 in an ATP- and/or ADP-dependent manner.

SUMMARY OF THE INVENTION

An endogenous protein, syntaxin, which is a member of the SNARE (soluble N-ethylmaleimide sensitive factor (NSF) attachment protein or SNAP receptor) superfamily of proteins originally described to mediate exocytosis,[9,10] has been found to bind to the nucleotide binding fold-1 (NBF1) and nucleotide binding fold-2 (NBF2) of sulfonyl urea receptors, SUR1 and SUR2A, in an adenine nucleotide-sensitive manner. Hence, this allows the development of assays for compounds that affect the binding of syntaxin to the NBFs of a SUR, and thus for compounds that modulate the $K_{ATP}$ channels of cells.

Accordingly, the present invention provides a method of screening for compounds that affect the binding between a syntaxin protein and a nucleotide binding fold-1 (NBF1) and/or nucleotide binding fold-2 (NBF2) comprising:

(a) contacting the syntaxin protein and the NBF1 and/or NBF2 in the presence of a test compound;

(b) determining the effect of the test compound on the binding of the syntaxin protein and the NBF1 and/or NBF2, wherein a difference in the binding between the syntaxin protein and the NBF1 and/or NBF2 in the presence of the test compound and the binding between the syntaxin protein and the NBF1 and/or NBF2 in the absence of the test compound (control) indicates that the compound affects the binding between the syntaxin protein and the NBF1 and/or NBF2.

The present invention also relates to a method of modulating a potassium ($K_{ATP}$) channel of a cell comprising administering an effective amount of a compound that affects the binding between a syntaxin protein and a NBF1 and/or NBF2 to a cell or animal in need thereof. The invention also includes a use of a compound that affects the binding between a syntaxin protein and a NBF1 and/or NBF2 to modulate a $K_{ATP}$ channel, as well as a use of a compound that affects the binding between a syntaxin protein and a NBF1 and/or NBF2 to prepare a medicament to modulate a $K_{ATP}$ channel.

The present invention also includes a method of modulating the potassium ($K_{ATP}$) channel of a cell comprising administering an effective amount of syntaxin, or an analog, homolog or mimetic thereof, or a fragment of syntaxin containing the NBF1 and/or NBF2 binding site, or an analog, homolog or fragment thereof, to a cell or animal in need thereof. The invention also includes a use of syntaxin, or an analog, homolog or mimetic thereof, or a fragment of syntaxin containing the NBF1 and/or NBF2 binding site, or an analog, homolog or fragment thereof, to modulate a $K_{ATP}$ channel, as well as a use of syntaxin, or an analog, homolog or mimetic thereof, or a fragment of syntaxin containing the NBF1 and/or NBF2 binding site, or an analog, homolog or fragment thereof, to prepare a medicament to modulate a $K_{ATP}$ channel.

The method of the invention, as applied to the modulation of membrane $K_{ATP}$ channels, may be useful in the treatment and/or prevention of any disease or condition that has as an underlying basis, a dysregulation of membrane $K_{ATP}$ channels. Examples of such diseases include, for example, type-1 or type-2 diabetes, cardiac arrhythmia, ischemic heart disease, coronary angina, hypertension, urinary incontinence, asthma, dysmenorrhea and irritable bowel syndrome, as well as diseases of the central nervous system (i.e. neurodegenerative diseases, schizophrenia, depression) and peripheral nervous system, skeletal muscles and endocrine cells.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 2 is the amino acid sequence of rat syntaxin-1A [SEQ ID NO: 1] with the predicted $H_3$ domain underlined.

FIG. 3A is an amino acid sequence comparison of NBF1 [SEQ ID NO: 2] and NBF2 [SEQ ID NO: 3] in the rat SUR1 with NBF1 [SEQ ID NO: 4] and NBF2 [SEQ ID NO: 5] in the rat SUR2A.

FIG. 3B is an amino acid sequence comparison of NBF1 and NBF2 in the rat SUR1 with NBF1 [SEQ ID NO: 6] and NBF2 [SEQ ID NO: 7] in the rat SUR2B.

FIG. 3C is an amino acid sequence comparison NBF1 and NBF2 in the rat SUR2A with NBF1 and NBF2 in the rat SUR2B.

FIG. 5A is a confocal micrograph showing syntaxin-1A on the plasma membrane of a cardiac muscle cell.

FIG. 5B is a Western blot showing the presence of syntaxin-1A in the enriched plasma membrane fraction of rat cardiac muscles.

Figure 1:
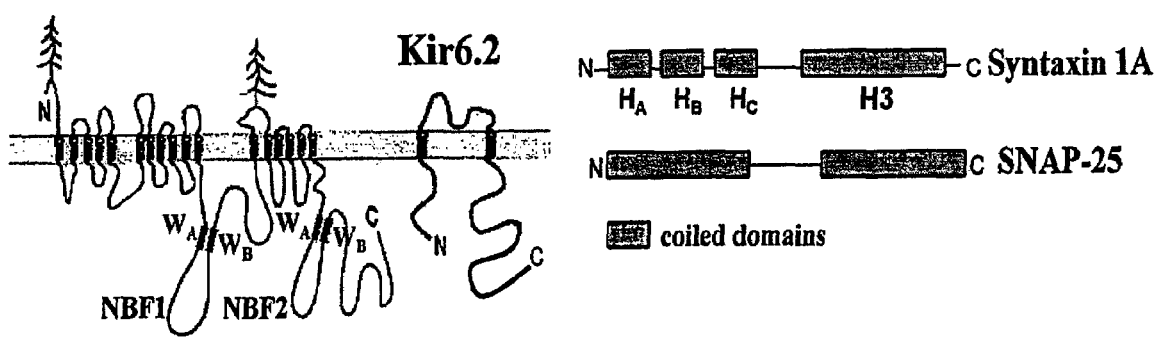
FIG. 1 contains a schematic of a membrane $K_{ATP}$ channel, including the SUR and Kir6.2 regions, as well as a schematic showing the domains of syntaxin-1A and SNAP-25.

DETAILED DESCRIPTION OF THE INVENTION (I) Assay for Modulators of Syntaxin-SUR Binding Syntaxin-1A has been found to bind and regulate the NBFs of a SUR in an ATP- and ADP-dependent manner. The present invention therefore includes methods of screening for compounds that affect the binding of syntaxin to NBF1 and/or NBF-2 of a SUR. A syntaxin protein, or a portion thereof, is contacted with a NBF1 and/or NBF2, or a portion thereof, in the presence and absence of a test compound. The effect of the test compound on the binding betweem the syntaxin protein and the NBF1 and/or NBF2 is measured. A compound is identified as effective if the binding between the syntaxin protein and the NBF1 and/or NBF2 is significantly different in the presence of the compound compared to in the absence of the test compound (control).

Accordingly, the present invention provides a method of screening for compounds that affect the binding between a syntaxin protein and a nucleotide binding fold-1 (NBF1) and/or nucleotide binding fold-2 (NBF2) comprising:

(a) contacting the syntaxin protein and the NBF1 and/or NBF2 in the presence of a test compound;

(b) determining the effect of the test compound on the binding of the syntaxin protein and the NBF1 and/or NBF2, wherein a difference in the binding between the syntaxin protein and the NBF1 and/or NBF2 in the presence of the test compound and the binding between the syntaxin protein and the NBF1 and/or NBF2 in the absence of the test compound (control) indicates that the compound affects the binding between the syntaxin protein and the NBF1 and/or NBF2.

The term "syntaxin" or "syntaxin protein" as used herein refers to a full length syntaxin protein or an analog, homolog or mimetic thereof, or fragment of a syntaxin protein containing the NBF1 and/or NBF2 binding site or an analog, homolog or mimetic thereof. It is to be understood that various amino acid changes, insertions, deletions, etc. may be made to a syntaxin protein without significantly altering its NBF1 and/or NBF2 binding site(s) and proteins having such changes are included within the definition of "syntaxin" and "syntaxin protein". Preferably the syntaxin protein is syntaxin-1A, or an analog, homolog or mimetic thereof, or fragment of a syntaxin-1A protein containing the NBF1 and/or NBF2 binding site(s) or an analog, homolog or mimetic thereof. The most likely interacting domains within syntaxin-1A are the α-helical coiled coil domains[26-30], particularly the syntaxin-1A H3 domain (Syn-1A$^{191-266}$). The amino acid sequence of rat syntaxin-1A is shown in FIG. 2 (SEQ ID NO: 1), with the predicted $H_3$ domain underlined. The amino acid sequence for other known syntaxin proteins is available in the art (see for example: Zhang R, Maksymowych A B, Simpson L L. Cloning and sequence analysis of a cDNA endoding a polypeptide essential for exocytosis. Gene 159:293-294, 1995. Genbank Accession no. L37792; and Strausberg R-Genbank no. BC000444)

The term "NBF1" and "NBF2" as used herein refer to the two nucleotide binding folds of a sulfonylurea receptor (SUR). The NBF1 domain spans aa 696-894 of SUR (1581 aa), with the Walker A ($W_A$) motif at aa 713-720, the Walker-B ($W_B$) motif at aa 850-854 and linker region at aa 721-849.[1,3] The NBF2 domain spans aa 1358-1536, with the $W_A$ motif at aa 1379-1386, the $W_B$ motif at aa 1502-1506, and linker region at aa 1387-1501. The term "NBF1" and "NBF2" domain also includes analogs, homologs and mimetics of NBF1 and NBF2 as well as fragments of the full length NBF1 and NBF2 proteins, which include the syntaxin binding site, and analogs, homologs and mimetics thereof. It is to be understood that various amino acid changes, insertions, deletions, etc. may be made to a NBF1 and/or NBF2 protein without significantly altering its syntaxin binding site and proteins having such changes are included within the definition of "NBF1" and "NBF2". The amino acid sequences of the NBF1 and NBF2 domains of the rat SUR1 (SEQ ID NO: 2 and SEQ ID NO:3, respectively) compared to the NBF1 and NBF2 domains of rat SUR2A (SEQ ID NO: 4 and SEQ ID NO:5, respectively) and rat SUR2B (SEQ ID NO: 6 and SEQ ID NO:7, respectively) are shown in FIGS. 3A-3B, respectively. A comparison of the amino acid sequences of the NBF1 and NBF2 domains of rat SUR2A and rat SUR2 is found in FIG. 3C. The amino acid sequence for other known the NBF1 and NBF2 domains of SURs are known in the art (see for example: Human SUR1: Thomas P M, Cote G C, Wohlik N, Haddad B, Mathew P M, Rabl W.,Aguilar-Bryan L, Gagel R F, Bryan J. Mutatin in the sulfonylurea receptor gene in familial hyperinsulinemic hypoglycemia of infancy. Science 268: 426-429, 1995; Human SUR2A: Chutkow et al. Cloning, tiossue expression, and chromosomal localization of SUR2, the putative drug-binding subunit of cardiac, skeletal muscle and vascular $K_{ATP}$ channels. Diabetes 45:1439-1445, 1996; Hamster SUR1: Aguilar-Bryan L, et al. Science 268:423-426, 1995; rat SUR2: Inagaki et al. Neuron 16:1011-1017, 1996).

A person having skill in the art would understand that the NBF1 and/or NBF2 proteins need not be derived from a sulfonylurea receptor. The NBF1 and/or NBF2 proteins or peptides should contain amino acid sequences that allow binding with the syntaxin protein. Preferably, NBF1 and/or NBF2 is derived from a sulfonylurea receptor selected from the group consisting of SUR1, SUR2A, SUR2B and SUR2C. Most preferably, NBF1 and/or NBF2 is derived from a sulfonylurea receptor selected from the group consisting of SUR1 and SUR2A.

The term "analog" as used herein includes, but is not limited, to amino acid sequences containing one or more amino acid substitutions, insertions, and/or deletions from a reference sequence. Amino acid substitutions may be of a conserved or non-conserved nature. Conserved amino acid substitutions involve replacing one or more amino acids of the proteins of the invention with amino acids of similar charge, size, and/or hydrophobicity characterisitics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics. Amino acid insertions may consist of single amino acid residues or sequential amino acids ranging from 2 to 15 amino acids in length. Deletions may consist of the removal of one or more amino acids, or discrete portions from the amino acid sequence. The deleted amino acids may or may not be contiguous.

The term homolog as used herein means that a particular subject sequence or molecule, has a degree of similarity with a reference sequence. For purposes of the present invention, amino acid sequences having greater than 90 percent similarity, equivalent biological activity, and equivalent expression characteristics are considered substantially homologous and are included within the scope of proteins defined by the terms "syntaxin", "syntaxin protein", "NBF1", "NBF2" and fragments thereof. Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

The term "mimetic" as used herein refers to proteins, polypeptides or peptides that mimic the effect of a subject protein, polypeptide or peptide. Syntaxin, or fragments thereof, may be used to identify specific conformational features required for the mimetic compound to interact with the NBF1 and/or NBF2 of a SUR. Standard approaches to determine the structure of syntaxin can also be used. These include a variety of nuclear magnetic resonance techniques, combined with various computational methods and/or X-ray crystallography. Using such standard approaches, compounds having sufficiently similar conformations can be produced and tested for their ability to affect the binding between a syntaxin protein and a NBF1 and/or NBF2 of a SUR. Once a particular desired conformation of a syntaxin protein has been ascertained, methods for designing a peptide or peptidomimetic to fit that conformation are well known in the art (see, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455). The design of peptide analogs may be further refined by considering the contribution of various side chains of amino acid residues (i.e., for the effect of functional groups or for steric considerations).

Accordingly, it is contemplated as being within the scope of the present invention to produce compounds that affect the binding between a syntaxin protein and a NBF1 and/or NBF2 of a SUR through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to as a "peptidomimetic", to designate substitutions or derivations from peptides found to be active, which possess the same backbone conformational features and/or other functionalities, so as to be sufficiently similar to the active peptides to affect the binding between a syntaxin protein and a NBF1 and/or NBF2 of a SUR.

The use of peptidomimetics for the development of high-affinity peptide/protein analogs is well known in the art (see, e.g., Zhao et al. (1995), Nature Structural Biology 2: 1131-1137; Beely, N. (1994), Trends in Biotechnology 12: 213-216; Hruby, V. J. (1993), Biopolymers 33: 1073-1082). Assuming rotational constraints similar to those of amino acid residues within a peptide, analogs comprising non-amino acid moieties may be analyzed, and their conformational motifs verified, by means of the Ramachandran plot (see Hruby & Nikiforovich, hereinabove), among other known techniques.

As hereinbefore mentioned, the NBF1, NBF2 and/or syntaxin protein should contain the amino acid sequences involved in the binding of syntaxin to the NBF1 and/or NBF2 of a SUR (i.e. the binding domains). A person skilled in the art would know how to determine the binding domains of the syntaxin protein and/or the NBF1 and/or NBF2 of a SUR. For example, recombinant proteins which divide NBF1, NBF2 and syntaxin into portions may be prepared and used in partner-capture assays. For example, the NBF domains may be divided into thirds [N-terminal third (NBF1N) 698-725 (includes $W_A$), linker region (NBF1L) 725-845, and C-terminal third (NBF1C) 846-885 (includes $W_B$) and correspondingly in NBF2: N-terminal third (NBF2N) 1365-1390 (includes $W_A$), linker region (NBF2L) 1390-1495, and C-terminal third (NBF2C) 1496-1540 (includes $W_B$)]. Each of the NBFs portions with one of the GST-proteins bound to glutathione agarose beads, may be incubated with full-length recombinant syntaxin proteins, and a 'pull down' study performed, followed by immuno-identification by Western analysis of the proteins pulled down by the beads as described in Example 1 herein. Conversely, full length NBF1 and/or NBF2 domains may be incubated with various portions of syntaxin with one of the GST-proteins bound to glutathione agarose beads, and a 'pull down' study performed, followed by immuno-identification by Western analysis of the proteins pulled down by the beads, as described in Example 1 herein. Similar experiments are described in U.S. Pat. No. 5,693,476 (the contents of which are incorporated herein by reference) in order to determine the binding sites for the syntaxin binding proteins, SNAP-25, alpha-SNAP, VAMP2 and n-sec1, on the syntaxin-1A protein.

The term "SUR" as used herein means a sulfonylurea receptor and includes all known SURs involved in modulating the $K_{ATP}$ channel of a cell in an adenine nucleotide-dependent manner. As hereinbefore stated, there are several isoforms of SUR.[1] SUR1A (1581 aa, 177 kDa) is the dominant isoform in pancreatic islets and brain,[3] SUR 2A[4,5] (1545 aa, 174 kD) in the heart and skeletal muscle, SUR2B[5,7] (1546 aa, 175 kD) in smooth muscle and vascular smooth muscle and the more ubiquitously expressed SUR2C (1512 aa, 170 kD).[1,5] Since there exists a high degree of homology between the NBF domains of the SURs (see background for details and FIGS. 3A-3C for actual amino acid sequence comparisons), and it has been shown herein that syntaxin binds to SUR1 and SUR2A, a person skilled in the art would understand that syntaxin should also bind to SUR2B and SUR2C.

The term "affect the binding between a syntaxin protein and a NBF1 and/or NBF2" means the test compound produces a difference in the binding between the syntaxin protein and the NBF1 and/or NBF2 in its presence as compared to the binding between the syntaxin protein and the NBF1 and/or NBF2 in its absence (control). Preferably this difference in binding is a significant difference. The compound may inhibit or enhance the binding, or in terms of the affect on the $K_{ATP}$ channel, act as an antagonist, an agonist or act as a compound which enhances the effects of other agonists or antagonists. A person having skill in the art could confirm that a compound that affects the binding between a syntaxin protein and a NBF1 and/or NBF2 also modulates the $K_{ATP}$ channel using standard assays, for example, whole-cell patch clamp assays using standard procedures, for example as described in Example 4 herein.

The term "significant" as used herein, specifically in terms of a "significant difference", refers to a difference in a quantifiable parameter between two groups being compared that is statistically-significant using standard statistical tests.

Methods for the production of recombinant proteins useful in the assays described herein are well known to a person skilled in the art. For example, polynucleotides encoding the syntaxin protein, NBF1, NBF2 or fragments thereof, may be cloned into an expression plasmid to produce the corresponding proteins. Recombinant plasmids can be transformed into appropriate strains of, for example, *E. coli* and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods.[31]

Isolated recombinant polypeptides produced as described above may be purified by standard protein purification procedures. These procedures may include differential precipitation, molecular sieve chromatography, ion-exchange chromatography, isoelectric focusing, gel electrophoresis and affinity chromatography.

In addition to recombinant methods, syntaxin or NBF proteins can be isolated from selected cells by affinity-based methods, such as by using appropriate antibodies. Further, syntaxin or NBF proteins may be chemically synthesized using methods known to those skilled in the art.

It will be understood that protein used as the "free" protein in a partner capture assay are synthesized so that they remain soluble during the binding assay. Proteins normally associated with lipid membranes, such as syntaxin, may be modified for increased solubility by, for example, expressing truncated versions ("cytoplasmic domains") of the proteins minus their membrane anchors.

The test compound can be any compound which one wishes to test including, but not limited to, proteins (including antibodies), peptides, nucleic acids (including RNA, DNA, antisense oligonucleotide, peptide nucleic acids), carbohydrates, organic compounds, inorganic compounds, natural products, library extracts, bodily fluids and other samples that one wishes to test for affecting the binding between a syntaxin protein and a NBF1 and/or NBF2 of a SUR. In particular the test compound may be a peptide mimetic of a syntaxin protein or a fragment thereof.

Methods of the present invention are well suited for screening libraries of compounds in multi-well plates (e.g., 96-well plates), with a different test compound or group of test compounds in each well. In particular, the methods may be employed with combinatorial libraries.

The method of the invention may be "miniaturized" in an assay system through any acceptable method of miniaturization, including but not limited to multi-well plates, such as 24, 48, 96 or 384-wells per plate, micro-chips or slides. The assay may be reduced in size to be conducted on a micro-chip support, advantageously involving smaller amounts of reagents and other materials. Any miniaturization of the process which is conducive to high-throughput screening is within the scope of the invention.

(a) Protein Interaction Binding Assays

A variety of approaches may be employed to assay the binding between a syntaxin protein and a NBF1 and/or NBF2 of a SUR. These include biochemical approaches (such as immobilized GST fusion protein constructs), bioassays (such as the yeast two-hybrid system), and physical biosensor assays (such as surface plasmon resonance). These assays are described in more detail below.

1. Biochemical Assays

Biochemical assays useful in the practice of the present invention include partner assays similar to those described above for the localization of syntaxin-binding sites on NBF1 and/or NBF2 (or vice versa). To identify a compound capable of affecting binding between a syntaxin protein to NBF1 and/or NBF2 of a SUR, a test compound is included in the solution (containing the "free" soluble protein; e.g., the syntaxin protein) that is contacted with the immobilized protein (e.g., the NBF1 and/or NBF2 of a SUR). The amount of bound syntaxin protein is detected and compared to the amount bound under similar conditions in the absence of the test compound (control). If the compound has a significant effect on the binding of syntaxin to the NBF1 and/or NBF2 (i.e., if the compound significantly increases or significantly decreases the binding), and the effect exceeds a threshold value (which is set to a desired level by the practitioner of the invention; e.g., several-fold increase or several-fold decrease in binding), the compound is identified as effective to affect or alter the binding of the syntaxin protein to NBF1 and/or NBF2 of a SUR.

It will be understood that various modifications of the above-described assay are included within the scope of the present invention. For example, the roles of the proteins can be switched—that is, the syntaxin protein may be immobilized to the solid support and a solution containing the NBF1 and/or NBF2 of a SUR may be contacted with the bound syntaxin protein. Additionally, the immobilized protein or the free protein may be exposed to a test compound prior to the binding assay, and the effects of this pre-exposure may be assessed relative to controls. Compounds identified in this manner also inhibit the binding of the syntaxin protein to NBF1 and/or NBF2 or vice versa. Alternatively, the test compound may be added subsequent to the mixing of the syntaxin protein and NBF1 and/or NBF2. A compound effective to reduce the level of binding in such an assay displaces the syntaxin protein from the NBF1 and/or NBF2, or vice versa.

In addition to Western blots, other, more rapid, detection schemes, such as multiwell ELISA-type approaches, may be employed. For example, a partially-purified (e.g., by the GST methods above) syntaxin protein may be attached to the bottoms of wells in a multiwell plate (e.g., 96-well plate) by introducing a solution containing the protein into the plate and allowing the protein to bind to the plastic. The excess protein-containing solution is then washed out, and a blocking solution (containing, for example, bovine serum albumin (BSA)) is introduced to block non-specific binding sites. The plate is then washed several more times and a solution containing an NBF1 and/or NBF2 of a SUR and, in the case of experimental (vs. control) wells, a test compound added. Different wells may contain different test compound, different concentrations of the same test substance, different syntaxin proteins or NBF1s or NBF2s, or different concentrations of syntaxin proteins or NBF1s or NBF2s. Further, it will be understood that various modifications to this detection scheme may be made. For example, the wells of a multiwell plate may be coated with a polypeptide containing the NBF1 and/or NBF2, rather than the syntaxin protein, and binding interactions assayed upon addition of a free syntaxin protein. The wells may also be precoated with compound(s) that enhance attachment of the protein to be immobilized and/or decrease the level of non-specific binding. For example, the wells may be derivatized to contain glutathione and may be pre-coated with BSA, to promote attachment of the immobilized protein in a known orientation with the binding site(s) exposed.

Detection methods useful in such assays include antibody-based methods (i.e., an antibody directed against the "free" protein), direct detection of a reporter moiety incorporated into the "free" protein (such as a fluorescent label), and proximity energy transfer methods (such as a radioactive "free" protein resulting in fluorescence or scintillation of molecules incorporated into the immobilized protein or the solid support).

Antibodies to syntaxin are known[9,10,28] and were used in Example 1 herein. A person skilled in the art would be able to prepare antibodies to syntaxin and the NBF1 and/or NBF2 of a SUR using well known procedures. For example, by using syntaxin, the NBF1 or NBF2 of a SUR, or homologs, analogs, mimetics, or fragments thereof, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975) as well as other techniques such as the human B-cell hybridoma technique (Kozbor et al., Immunol. Today 4, 72 (1983), the EBV-hybridoma technique to produce human monoclonal antibodies (Cole et al., Monoclonal Antibodies in Cancer Therapy (1985) Allen R. Bliss, Inc., pages 77-96), and screening of combinatorial antibody libraries (Huse et al., Science 246, 1275 (1989))

2. Yeast Two-Hybrid Assays

The yeast two-hybrid protein interaction assay may also be employed to identify compounds that affect the binding of a syntaxin protein to a NBF1 and/or NBF2 of a SUR. The assay is based on the finding that most eukaryotic transcription activators are modular (see for e.g, Brent, et al.[32]), i.e., that the activators typically contain activation domains that activate transcription, and DNA binding domains that localize the activator to the appropriate region of a DNA molecule.

In a two hybrid system, a first fusion protein contains one of a pair of interacting proteins fused to a DNA binding domain, and a second fusion protein contains the other of a pair of interacting proteins fused to a transcription activation domain. The two fusion proteins are independently expressed in the same cell, and interaction between the "interacting protein" portions of the fusions reconstitute the function of the transcription activation factor, which is detected by activation of transcription of a reporter gene.

At least two different cell-based two hybrid protein-protein interaction assay systems have been used to assess binding interactions and/or to identify interacting proteins. Both employ a pair of fusion hybrid proteins, where one of the pair contains a first of two "interacting" proteins fused to a transcription activation domain of a transcription activating factor, and the other of the pair contains a second of two "interacting" proteins fused to a DNA binding domain of a transcription activating factor.

The yeast GAL4 two hybrid system[33-36] was developed to detect protein-protein interaction based on the reconstitution of function of GAL4, a transcriptional activator from yeast, by activation of a GAL1-lacZ reporter gene. Like several other transcription activating factors, the GAL4 protein contains two distinct domains, a DNA binding domain and a transcription activation domain. Each domain can be independently expressed as a portion of a fusion protein composed of the domain, and a second, "bait" interacting protein. The two fusion proteins are then independently expressed together in a cell. When the two GAL4 domains are brought together by a binding interaction between the two "interacting" proteins, transcription of a reporter gene under the transcriptional control of GAL4 is initiated. The reporter gene typically has a promoter containing GAL4 protein binding sites (GAL upstream activating sequences, UAS.sub.G).

A two hybrid system such as is described above may be used to identify compounds effective to affect the binding of a syntaxin protein to a NBF1 and/or NBF2 of a SUR as follows. A polynucleotide encoding a syntaxin protein is fused to the GAL4 DNA binding domain (G4BD) in a yeast expression vector. The vector is used to generate yeast cells harboring the expression vector and a GAL4-activated reporter gene (e.g., LacZ). These cells are then transformed with a vector carrying a fusion between the transcription activating domain of yeast GAL4 (G4AD) and a NBF1 and/or NBF2 or a SUR. Transformants are screened (e.g., using a β-galactosidase (β-gal) assay on plates containing the chromogenic substrate X-gal) for expression of the reporter. Reporter-expressing cells are selected, cloned, and used to screen test compounds. Compounds which increase or decrease reporter expression relative to a user-defined threshold (e.g., five-fold increase or five-fold decrease) are identified as affecting binding of the syntaxin protein to a NBF1 and/or NBF2 of a SUR.

A second two hybrid system, described in detail in Ausubel, et al.,[31] utilizes a native E. coli LexA repressor protein which binds tightly to appropriate operators. A plasmid is used to express one of a pair of interacting proteins (the "bait" protein) as a fusion to LexA.

The plasmid expressing the LexA-fused bait protein is used to transform a reporter strain of yeast, such as EGY48. In this strain, binding sites for LexA are located upstream of two reporter genes. In the first reporter system, the upstream activation sequences of the chromosomal LEU2 gene, required in the biosynthetic pathway for leucine (Leu), are replaced in EGY48 with lexA operators, permitting selection for viability when cells are plated on medium lacking Leu. In the second reporter system, EGY48 harbors a plasmid, pSH18-34, that contains a lexA operator-lacZ fusion gene, permitting discrimination based on color when the yeast is grown on medium containing Xgal.[31]

LexA and GAL4 each have different properties that should be considered when selecting a system. LexA is derived from a heterologous organism, has no known effect on the growth of yeast, possesses no residual transcriptional activity, can be used in GAL4.sup.+yeast, and can be used with a Gal-inducible promoter. Because GAL4 is an important yeast transcriptional activator, experiments must be performed in gal4 yeast strains to avoid background from endogenous GAL4 activating the reporter system. Both two hybrid systems have been successfully used for isolating genes encoding proteins that bind a target protein and as simple protein binding assays,[37,38] and both can be applied to the identification of compounds capable of affecting binding of a syntaxin protein to a NBF1 and/or NBF2 of SUR.

3. Biosensor-Based Assays

Yet another method of identifying a compound capable of affecting binding of a syntaxin protein to a NBF1 and/or NBF2 of SUR is through the use of affinity biosensor methods. Such methods may be based on the piezoelectric effect,[39-43] electrochemistry[44] or optical methods, such as ellipsometry,[45-47] optical wave guidance[43] and surface plasmon resonance (SPR).[49-50] SPR is particular advantageous for monitoring molecular interactions in real-time, enabling a sensitive and comprehensive analysis of the effects of test compounds on the binding interactions between two proteins than the methods discussed above. This advantage is somewhat offset, however, by the lower throughput of the technique (as compared with multiwell plate -based methods).

4. Functional Assays

Compounds identified as having an effect on the binding between a syntaxin protein and a NBF1 and/or NBF2 of a SUR using an assay described above, may be further evaluated for their effect on the $K_{ATP}$ channel activity as well as the effect of ATP/ADP concentration on this activity. For example, whole-cell patch clamp assays may be employed using standard assays, for example, as described in Example 4 herein.

(b) Determining the Extent of Binding

The type of measurement used to quantify the effect of a test compound on the binding between a syntaxin protein and a NBF1 and/or NBF2 of a SUR will depend on the type of assay and detection methods used and this can be readily determined by a person having skill in the art. For example, when using a biological screen that employs Western blotting as the means for detection, the binding can be measured using densitometry. The densitometry values may be normalized and a threshold level may be set based on the amount of variation in the signal between a series of control samples (i.e. without test compound). The smaller the variation, the smaller the effect of a test compound that can be reliably detected.

As hereinbefore mentioned, a test compound can be said to have an effect on the binding between a syntaxin protein and a NBF1 and/or NBF2 of a SUR if the compound has any effect on the binding of syntaxin to the NBF1 and/or NBF2 (i.e., if the compound increases or decreases the binding), and the effect exceeds a threshold value (which is set to a desired level by the practitioner of the invention as described above; e.g., several-fold increase or several-fold decrease in binding). Preferably the effect on binding is a significant effect.

The term "significant" as used herein, specifically in terms of a "significant effect", refers to a difference in a quantifiable parameter between two groups being compared that is statistically-significant using standard statistical tests.

Therefore, in an embodiment of the present invention, there is provided a method of screening for compounds that affect the binding between a syntaxin protein and a NBF1 and/or NBF2 comprising:

(a) contacting the syntaxin protein and the NBF1 and/or NBF2 in the presence of a test compound;

(b) determining the effect of the test compound on the binding of the syntaxin protein and the NBF1 and/or NBF2; and (c) identifying the compound as effective if its measured effect on the extent of binding is above a threshold level.

Preferably, NBF1 and/or NBF2 is derived from a sulfonylurea receptor selected from the group consisting of SUR1, SUR2A, SUR2B and SUR2C. Most preferably, NBF1 and/or NBF2 is derived from a sulfonylurea receptor selected from the group consisting of SUR1 and SUR2A.

(c) Kits

The development of the screening assay of the invention allows the preparation of kits for use in identifying compounds that affect the binding of a syntaxin protein and NBF1 and/or NBF2 of a SUR. The kits would comprise the reagents suitable for carrying out the methods of the invention, packaged into suitable containers and providing the necessary instructions for use.

Accordingly, the present invention includes a kit for use in identifying a compound that affects the binding of a syntaxin protein and NBF1 and/or NBF2 of a SUR comprising an aliquot of a syntaxin protein and an aliquot of a NBF1 and/or NBF2. Preferably, NBF1 and/or NBF2 is derived from a sulfonylurea receptor selected from the group consisting of SUR1, SUR2A, SUR2B and SUR2C. Most preferably, NBF1 and/or NBF2 is derived from a sulfonylurea receptor selected from the group consisting of SUR1 and SUR2A.

In embodiments of the present invention, the reagents comprise at least the binding sites of the syntaxin protein and the NBF1 and/or NBF2 of a SUR. Either or both of the syntaxin protein and the NBF1 and/or NBF2 of a SUR may be attached to a solid support, for example glutathione beads. The kit may also include aliquots of the appropriate reagents for monitoring the binding of a syntaxin protein and NBF1 and/or NBF2 of a SUR using any of the methods described above, for example, antibodies which specifically bind to either or both of the syntaxin protein and the NBF1 and/or NBF2 of a SUR. The production and availability of antibodies to a syntaxin protein and a NBF1 and/or NBF2 of a SUR is described herein above. The kit may provide instructions for carrying out the assay of the invention.

With particular regard to assay systems packaged in "kit" form, it is preferred that assay components be packaged in separate containers, with each container including a sufficient quantity of reagent for at least one assay to be conducted. A preferred kit is typically provided as an enclosure (package) comprising one or more containers for the within-described reagents.

The reagents as described herein may be provided in solution, as a liquid dispersion or as a substantially dry powder, e.g., in lyophilized form. Usually, the reagents are packaged under an inert atmosphere.

Printed instructions providing guidance in the use of the packaged reagent(s) may also be included, in various preferred embodiments. The term "instructions" or "instructions for use" typically includes a tangible expression describing the reagent concentration or at least one assay method parameter, such as the relative amounts of reagent and sample to be admixed, maintenance time periods for reagent/sample admixtures, temperature, buffer conditions, and the like.

(II) Uses (a) Therapeutic Applications

It has been found that syntaxin-1A binds to NBF1 and NBF2 of SUR1 in an adenine nucleotide-dependent manner. Syntaxin-1A has also been shown to bind to NBF1 and NBF2 of SUR2A. The NBF1s and NBF2s are very well conserved between the SUR1 and SUR2 isoforms (see background and FIGS. 3A-3C), therefore, compounds generated to affect the binding of syntaxin to the NBF1 and NBF2 of SUR1, are likely to also interact with the NBF1 and NBF2 of the SUR2 isoforms. Such compounds will modulate (sensitize or desensitize) the interactions of the SUR protein of the specific cell type to the specific drugs acting on the variable N-terminal domains (i.e. sulfonylureas, potassium channel openers (KCOs)[24,25]) and the very C-terminal end of each of the SUR isoforms. This gives rise to the opportunity of the use of designer combinatorial drug treatments where sensitization, selectivity and potency of drug actions are conferred by different drugs within each combination. For example, there are KCOs, some already used clinically, which selectively act on the respiratory smooth muscle, urinary bladder and coronary arteries.[25] Administration of recombinant syntaxin-1A to rat islet β-cells has also been shown to inhibit $K_{ATP}$ activity in an adenine nucleotide-dependent manner.

Compounds that affect the binding between a syntaxin protein and a NBF1 and/or NBF2 of a SUR can offer unique therapies for diseases or conditions that have as an underlying basis, a dysregulation of membrane $K_{ATP}$ channels. Such therapies would possess superior therapeutic features of high efficacy, physiologic sensitivity and specificity.

Accordingly, the present invention includes a method of modulating a potassium ($K_{ATP}$) channel of a cell comprising administering an effective amount of a compound that affects the binding between a syntaxin protein and a NBF1 and/or NBF2 to a cell or animal in need thereof. The invention also includes a use of a compound that affects the binding between a syntaxin protein and a NBF1 and/or NBF2 to modulate the $K_{ATP}$ channel as well as a use of a compound that affects the binding between a syntaxin protein and a NBF1 and/or NBF2 to prepare a medicament to modulate the $K_{ATP}$ channel.

The invention also includes a method of treating a disease or condition that has as an underlying basis, a dysregulation of membrane $K_{ATP}$ channels, comprising administering an effective amount of a compound that affects the binding between a syntaxin protein and a NBF1 and/or NBF2 to a cell or animal in need thereof. The invention also includes a use of a compound that affects the binding between a syntaxin protein and a NBF1 and/or NBF2 to treat a disease or condition that has as an underlying basis, a dysregulation of membrane $K_{ATP}$ channels as well as a use of a compound that affects the binding between a syntaxin protein and a NBF1 and/or NBF2 to prepare a medicament to treat a disease or condition that has as an underlying basis, a dysregulation of membrane $K_{ATP}$ channels.

The present invention also includes a method of modulating the potassium ($K_{ATP}$) channel of a cell comprising administering an effective amount of syntaxin, or an analog, homolog or mimetic thereof, or a fragment of syntaxin containing the NBF1 and/or NBF2 binding site, or an analog, homolog or fragment thereof, to a cell or animal in need thereof. The invention also includes a use of syntaxin, or an analog, homolog or mimetic thereof, or a fragment of syntaxin containing the NBF1 and/or NBF2 binding site, or an analog, homolog or fragment thereof, to modulate a $K_{ATP}$ channel, as well as a use of syntaxin, or an analog, homolog or mimetic thereof, or a fragment of syntaxin containing the NBF1 and/or NBF2 binding site, or an analog, homolog or fragment thereof, to prepare a medicament to modulate a $K_{ATP}$ channel.

In a further embodiment of the present invention, the $K_{ATP}$ channel activity may be distinctly modulated by adenine nucleotides as a direct result of the binding of a compound that affects the binding between a syntaxin protein and a NBF1 and/or NBF2 of a sulfonylurea receptor (SUR).

Examples of diseases of conditions that may have as an underlying basis, a dysregulation of membrane $K_{ATP}$ channels include, for example, type-1 or type-2 diabetes, cardiac arrhythmia, ischemic heart disease, coronary angina, hypertension, urinary incontinence, asthma, dysmenorrhea and irritable bowel syndrome as well as diseases of the central nervous system (i.e. neurodegenerative diseases, schizophrenia, depression) and peripheral nervous system, skeletal muscles and endocrine cells.

Preferably, NBF1 and/or NBF2 is derived from a sulfonylurea receptor selected from the group consisting of SUR1, SUR2A, SUR2B and SUR2C. Most preferably, NBF1 and/or NBF2 is derived from a sulfonylurea receptor selected from the group consisting of SUR1 and SUR2A.

Diabetes is caused by a failure of the pancreatic islet β-cells to secrete insulin. The major class of drugs used to treat diabetes, called sulfonylureas, directly activate SUR1 in a manner independent of changes in ATP/ADP ratio and therefore also of changes in serum glucose concentrations. This results in inappropriate release of insulin even when blood glucose levels are low (i.e. during fasting), and this would result in life-threatening hypoglycemia and related symptoms. It is therefore ideal to identify a drug target capable of stimulating the islet β-cell to release insulin in a glucose-sensitive manner. Such compounds will be capable of increasing insulin secretion in a glucose-dependent manner through their physical and functional interactions with either one or both NBFs of the pancreatic islet SUR1 protein. Such compounds will also confer increased glucose-sensitivity specifically to pancreatic islet β-cells since glucose-evoked changes in ATP/ADP ratio is specific to the insulin-secreting islet beta cell.

Therefore in a specific embodiment of the present invention, there is provided a method of treating diabetes comprising administering an effective amount of a compound that affects the binding between a syntaxin protein and a NBF1 and/or NBF2 of SUR1 to a cell or animal in need thereof. The invention also includes a use of a compound that affects the binding between a syntaxin protein and a NBF1 and/or NBF2 of SUR1 to treat diabetes as well as a use of a compound that affects the binding between a syntaxin protein and a NBF1 and/or NBF2 of SUR1 to prepare a medicament to treat diabetes. In order to increase insulin secretion in a glucose-dependent manner, it is preferred that the compound that affects the binding of a syntaxin protein and a NBF1 and/or NBF2 of SUR1 is an agonist, or increases the binding of the syntaxin protein to the NBF1 and/or NBF2 of SUR1.

The compounds that affect the binding between a syntaxin protein and a NBF1 and/or NBF2 of SUR1 can be used in combination with drug molecules which act directly on (i.e. sulfonylureas) or modify (i.e. phosphorylation) the SUR1 protein, or the Kir6.2 subunit, as well as drug molecules which modify the ATP or ADP levels. These types of drugs will increase the potency of drug action by compounds that affect the binding between a syntaxin protein and a NBF1 and/or NBF2 of SUR1. An example is a combination of a compound that affects the binding of a syntaxin protein and the NBF1 and/or NBF2 of SUR1 with a low-dose of sulfonylurea or similar drugs, including naturally-occurring and synthetic incretin hormones such as glucagon-like peptides. This unique combination therapy for diabetes will possess not only superior therapeutic features of high efficacy, physiologic glucose-sensitivity, and specificity, but also low side effects (hypoglycemia, accelerated islet death or apoptosis, cardiovascular complications, and others) by avoiding the need to use high doses of these drugs (i.e. sulfonylureas).

Therapeutic antagonists to the binding of a syntaxin protein to a NBF1 and/or NBF2 of SUR1 can be developed to block the effects of syntaxin on the NBFs of SUR1 in the islet β-cells. This can be a potential treatment for hyper-insulin secretory disorders.

Other molecules (i.e. SNAP-25, Munc18, Munc13, VAMP, synaptotagmin, etc.) which interact with the syntaxin protein can further modulate these protein actions on the SUR protein. Drug molecules can be developed to mimic the actions of these syntaxin-modulating molecules.

In further specific embodiments of the present application, it has been shown that syntaxin-1A binds to SUR2A. The cardiac muscle, which possesses SUR2A, a functionally distinct protein from islet β-cell SUR1. This finding is of high therapeutic importance since the opening of cardiac $K_{ATP}$ channels protects the myocardium from damage during ischemia, whereby the resulting shortening of the action potential reduces $Ca^{2+}$ influx and energy consumption.[2,13] Currently, there are very limited pharmacological therapies (i.e. $K^+$ channel openers-KCOs) available for cardiac ischemia, primarily because of the lack of specific drug targets. The present invention therefore provides a novel drug target which will lead to the development of a whole new class of drugs, with selective agonist and antagonist actions which could be used independently or in combination with tissue-specific potassium channel openers (KCOs) to protect the cardiac muscle from ischemic injury, and possibly for more effective control of cardiac muscle failure and arrhythmias. SUR2B, a spliced variant of SUR2A, controls the $K_{ATP}$ channels in vascular smooth muscles to maintain muscle tone. SUR2B-$K_{ATP}$ channel opening by these novel therapeutic strategies could therefore also induce vasodilation to treat coronary angina and hypertension.

Accordingly, in a further specific embodiment, the present invention, includes a method to treat a disease or condition selected from the group consisting of cardiac ischemia, cardiac arrhythmia, coronary angina and hypertension, comprising administering an effective amount of a compound that affects the binding between a syntaxin protein and a NBF1 and/or NBF2 of a SUR2 to a cell or animal in need thereof. The invention also includes a use of a compound that affects the binding between a syntaxin protein and a NBF1 and/or NBF2 of SUR2 to treat a disease or condition selected from the group consisting of cardiac ischemia, cardiac arrhythmia, coronary angina and hypertension, as well as a use of a compound that affects the binding between a syntaxin protein and a NBF1 and/or NBF2 of SUR2A to prepare a medicament to treat a disease or condition selected from the group consisting of cardiac ischemia, cardiac arrhythmia, coronary angina and hypertension. The compound may be administered alone or in combination with other known tissue-specific potassium channel openers. In order to treat cardiac ischemia, cardiac arrhythmia, coronary angina and hypertension, it is preferred that the compound that affects the binding between a syntaxin protein and a NBF1 and/or NBF2 of a SUR2 be an antagonist, i.e. a compound that opens the $K_{ATP}$ channel.

The compound that affects the binding between a syntaxin protein and a NBF1 and/or NBF2 of a sulfonylurea receptor (SUR) may include, but is not limited to, proteins (including antibodies), peptides, nucleic acids (including RNA, DNA, antisense oligonucleotide, peptide nucleic acids), carbohydrates, organic compounds, inorganic compounds, natural products, library extracts, bodily fluids and other samples that affects the binding of a syntaxin protein to a NBF1 and/or NBF2 of a SUR. In particular the test compound may be a peptide mimetic of a syntaxin protein or a fragment thereof. In preferred embodiments, the compound is identified using one of the screening assays described herein.

The term "affect the binding between a syntaxin protein and a NBF1 and/or NBF2" means the test compound produces a difference in the binding between the syntaxin protein and the NBF1 and/or NBF2 in its presence as compared to the binding between the syntaxin protein and the NBF1 and/or NBF2 in its absence (control). Preferably this difference in binding is a significant difference. The compound may inhibit or enhance the binding, or in terms of the affect on the $K_{ATP}$ channel, act as an antagonist, an agonist or act as a compound which enhances the effects of other agonists or antagonists. A person having skill in the art could confirm that a compound that affects the binding between a syntaxin protein and a NBF1 and/or NBF2, also modulates the $K_{ATP}$ channel using standard assays, for example, whole-cell patch clamp assays using standard procedures, for example as described in Example 4 herein.

The term "effective amount" as used herein is defined as an amount effective, at dosages and for periods of time necessary to achieve the desired result. The effective amount of a compound of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity as well as the enhancement of a function or activity.

To "inhibit" or "suppress" or "reduce" a function or activity is to reduce the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

The invention extends to any compound that affects the binding between a syntaxin protein and a NBF1 and/or NBF2 of a SUR using the methods of the invention. The invention also includes a pharmaceutical composition comprising a compound that affects the binding between a syntaxin protein and a NBF1 and/or NBF2 of a SUR identified using the screening method of the invention in admixture with a suitable diluent or carrier. The invention further includes a method of preparing a pharmaceutical composition for use in affecting the binding between a syntaxin protein and a NBF1 and/or NBF2 of a SUR comprising mixing a compound identified using the screening assay of the invention with a suitable diluent or carrier.

The compounds the affect the binding between a syntaxin protein and a NBF1 and/or NBF2 of a SUR (including those identified using the methods described herein) may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effect. The substances may be administered to living organisms including humans and animals. Dosage regime may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Merck Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

(b) Drug Discovery Business Methods

The present invention also includes all business applications of the screening assay of the invention including conducting a drug discovery business.

Accordingly, the present invention also provides a method of conducting a drug discovery business comprising:

(a) providing a method for identifying compounds that affect the binding between a syntaxin protein and a NBF1 and/or NBF2 of a SUR according to the present invention;

(b) conducting therapeutic profiling of compounds identified in step (a), or further analogs thereof, for efficacy and toxicity in animals; and (c) formulating a pharmaceutical preparation including one or more compounds identified in step (b) as having an acceptable therapeutic profile.

In certain embodiments, the subject method can also include a step of establishing a distribution system for distributing the pharmaceutical preparation for sale, and may optionally include establishing a sales group for marketing the pharmaceutical preparation.

The present invention also provides a method of conducting a target discovery business comprising:

(a) providing a method for identifying compounds that affect the binding between a syntaxin protein and a NBF1 and/or NBF2 of a SUR according to the present invention;

(b) (optionally) conducting therapeutic profiling of compounds identified in step (a) for efficacy and toxicity in animals; and (c) licensing, to a third party, the rights for further drug development and/or sales for compounds identified in step (a), or analogs thereof.

By method of identifying compounds, it is meant, the equipment, reagents and methods involved in conducting a screen of compounds for the ability to affect the binding between a syntaxin protein and a NBF1 and/or NBF2 of a SUR using the methods of the present invention.

The following non-limiting examples are illustrative of the present invention:

EXAMPLES

Example 1

Nucleotide Binding Fold 1 (NBF-1) and NBF-2 of Both SUR-1 and SUR-2A Directly Bind Syntaxin-1A (Syn-1A)

GST (control) or GST-NBF-1 or GST-NBF-2 (375 pmol protein)of SUR-1 or SUR-2A, bound to glutathione beads, was incubated with Syn-1A or SNAP-25 (375 pmol protein) in 25 mM Hepes (pH 7.4) with 50 mM NaCl, 0.1% gelatin, 0.1% Triton X-100, 0.1% BSA and 0.2% β-mercaptoethanol at 4° C. for 2 hours. Following washing the beads three times with 20 mM Hepes(pH 7.4) with 150 mM KoAc, 1 mM EDTA, 1 mM $MgCl_2$, 5% glycerol and 0.1% Triton X-100, the samples were subjected to 15% SDS-PAGE, transferred to nitrocellulose membrane and probed with antibody against Syn-1A (1:2000) or SNAP-25 (1:1000).

Results: NBF-1 and NBF-2 of SUR1 (shown in FIG. 6A) and of SUR2A (shown in FIG. 6B) directly 'pulled' down Syntaxin 1A, and therefore the binding of these proteins are direct. This binding is specific since GST and GST-SNAP-25 did not pull down the NBF-1 or NBF-2 of either SUR1 or SUR2A.

Example 2

Syntaxin-1A is Located on the Plasma Membrane of Rat Cardiac Muscle Cells

Figure 7:
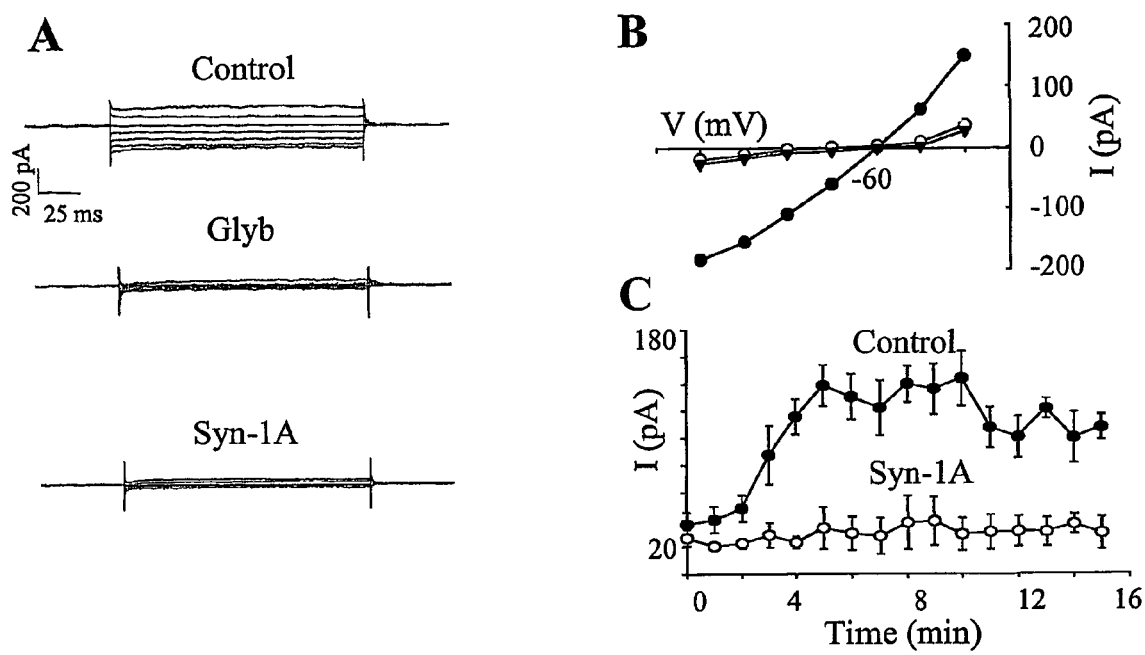
FIG. 7A shows representative $K_{ATP}$ whole cell patch-clamp currents from the freshly isolated rat pancreatic β-cells in the absence (control) and presence of recombinant syntaxin-1A.
FIG. 7B s a graph showing the corresponding current-voltage (I-V) relationships from the control and syntaxin-1A-treated rat pancreatic β-cells.
FIG. 7C is a graph showing the inhibitory effect of the recombinant syntaxin-1A on the mean $K_{ATP}$ whole cell currents.

Confocal microscopy shows that syntaxin-1A is located on the plasma membrane of a cardiac muscle cell (see FIG. 7A). Syntaxin-1A was also found in the purified enriched plasma membrane fraction of rat cardiac muscles (see FIG. 7B). 100 mg protein of plasma membrane fraction, with rat brain homogenates (5 mg) used as a positive control, was separated by SDS-PAGE, and the separated proteins identified by anti-syntaxin antibodies. In FIG. 7B syntaxin-1A (black arrow) and syntaxin-1B (white arrow) are identified.

Example 3

Figure 6:
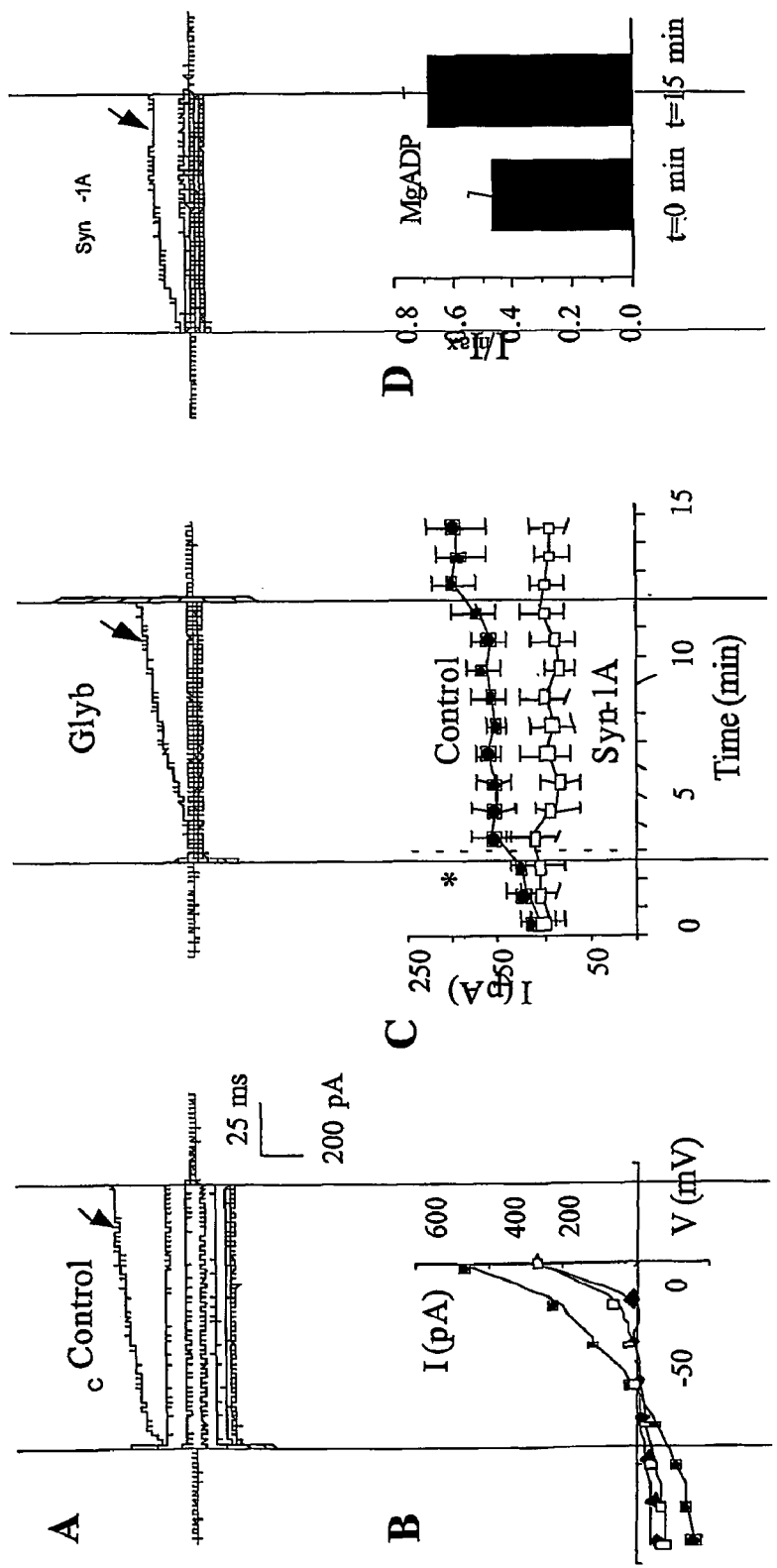
FIG. 6A shows representative $K_{ATP}$ whole cell patch-clamp currents from the control and syntaxin-1A-overexpressing HIT cells.
FIG. 6B is a graph showing the corresponding current-voltage (I-V) relationships from the control and syntaxin-1A-overexpressing HIT cells.
FIG. 6C is a graph showing the inhibitory effect of syntaxin-1A on the mean $K_{ATP}$ whole cell currents.
FIG. 6D is a bar graph showing the effect of Mg-ADP on the $K_{ATP}$ whole cell currents in cells overexpressing syntaxin-1A.

Syntaxin 1A Modulates Insulinoma HIT Cell $K_{ATP}$ Channel Activity in an ATP- and ADP-Dependent Manner Representative $K_{ATP}$ whole-cell patch-clamp currents recorded from the control and syntaxin-1A overespressing HIT cells are shown in FIG. 6A. Cells were stimulated by voltage steps from −140 to 0 mV from a holding potential of −50 mV. Glybenclamide (0.1 mM) reduced the current amplitude in the control cell (n=4). The currents recorded from the HIT cell transfected with syntaxin-1A were also reduced compared with the control cells (n=10). Arrows show the presence of another type of $K^+$ current (a large conductance outward current) activated at 0 mV. The corresponding current-voltage (I-V) relationships and shown in FIG. 6B: (filled circles) control, (diamonds) glybenclamide, (open circles) syntaxin-1A. All currents were recorded 15 min after the formation of the whole-cell configuration when a cell interior exchanged with the pipette solution containing low (0.3 mM) ATP concentration. The inhibitory effect of syntaxin-1A on the mean $K_{ATP}$ whole cell-currents (mean±SEM; n=10 for syntaxin-1A and n=9 for control) measured at −140 mV and recorded for 15 minutes are shown in FIG. 6C. An asterisk indicates the first minutes of recording after obtaining the whole-cell configuration. The effect of Mg-ADP on the $K_{ATP}$ whole cell-currents in cells overexpressing syn-1A are shown in FIG. 6D. Pipette solution contains 3 mM MgADP and only 0.3 mM ATP. Compared with the currents measured just after formation of the whole-cell configuration (t=0 min), the whole cell currents (mean±SEM; n=5) measured at 15th minute of the recording (t=15 min) were increased due to dialysis of MgADP. Currents were measured at −120 mV, and normalized to the maximal current ($I_{max}$).

Figure 4:
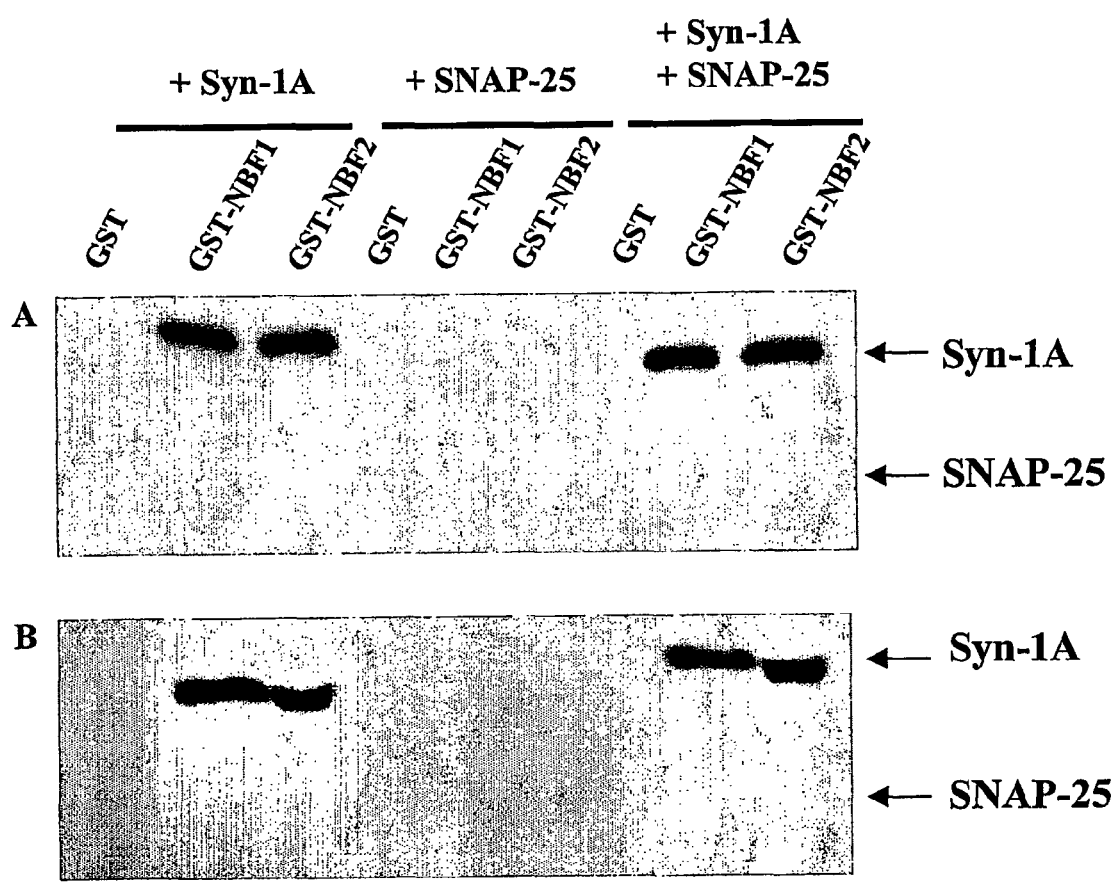
FIG. 4A is a Western blot showing the binding of syntaxin-1A and NBF1 and NBF2 of SUR1.
FIG. 4B is a Western blot showing the binding of syntaxin-1A and NBF1 and NBF2 of SUR2A.

Results. $K_{ATP}$ channel activity in insulinoma HIT cells was first confirmed using patch-clamp techniques and showed its typical glybenclamide sensitivity (FIG. 6A). The functional interaction of syntaxin-1A with SUR1/$K_{ATP}$ complex was then examined. FIGS. 4A, 4B and 4C show the inhibitory effects of syntaxin-1A overexpression (>3 fold by Western analysis) in HIT cells on the endogenous $K_{ATP}$ whole-cell currents. This inhibitory effect was observed only with the low concentration of ATP (0.3 mM) in the patch pipette. FIG. 6C shows the time-course of the $K_{ATP}$ whole-cell current in control and syntaxin-1A overexpressing cells. Just after the formation of the whole-cell configuration (t=0 min), the $K_{ATP}$ currents were similar in both types of cells (see asterisk). After 3 min, the control currents increased steadily in time due to the exchange of low (0.3 mM) pipette [ATP] with the cell interior. At t=15 min, the control current was increased by 100% of the current at t=0 min. However, in syntaxin-1A overexpressing cells, the current remained unchanged (FIG. 6C). It was concluded that syntaxin-1A inhibitory effects on $K_{ATP}$ were present at low [ATP], but was not manifested at normal cytoplasmic ~1 mM ATP levels (see asterisk). FIG. 6D shows the effect of MgADP on $K_{ATP}$ whole-cell currents in syntaxin-1A overexpressing cells at low [ATP] (0.3 mM). Remarkably, MgADP (3 mM) partially reversed the inhibitory effects of syntaxin-1A on the $K_{ATP}$ currents. At t=15 min, the syntaxin-1A inhibited current was reversed by 46% compared with the current at t=0 min (FIG. 6D). Conclusion. These results show that the syntaxin 1A effects on $K_{ATP}$ channel activity are manifested at low ATP concentrations and can be reversed by high ADP concentrations.

Example 4

Syntaxin-1A Inhibits Rat Islet Beta Cell $K_{ATP}$ Channel Activity in an ATP-Dependent Manner Representative $K_{ATP}$ whole-cell patch-clamp currents recorded from the freshly isolated rat pancreatic beta cells in the absence (control) and presence of recombinant syntaxin-1A protein are shown in FIG. 7A. Cells were stimulated by voltage steps from −140 to −20 mV (or 0 mV) from a holding potential of −50 mV. Glybenclamide (0.1 mM) applied to the cell exterior reduced the current amplitude in the control cells (n=4). Recombinant syntaxin-1A ($10^{-3}$ M) was dialyzed into the cell interior through the patch pipette. The currents recorded from the beta cell dialyzed with syntaxin-1A (n=4) were also reduced compared with the control beta cells (n=5). In FIG. 7B, corresponding current-voltage (I-V) relationships are shown: (filed circles) control, (diamonds) glybenclamide, (open circles) syntaxin-1A. All currents were recorded 15 min after the formation of the whole-cell configuration when a cell interior exchanged with the pipette solution containing low (0.3 mM) ATP concentration that under control conditions opens the $K_{ATP}$ channel. The inhibitory effect of the recombinant syntaxin-1A protein on the mean $K_{ATP}$ whole cell-currents (mean±SEM; n=4 for syntaxin-1A and n=5 for control) measured at −120 mV and recorded for 15 minutes is depicted in FIG. 7C. Despite the presence of 0.3 mM ATP in the patch pipette which opened the $K_{ATP}$ channels in Control cells, syntaxin-1A still strongly inhibits the activity of the channel. The inhibitory effects of syntaxin-1A on $K_{ATP}$ channels are therefore manifested in low ATP concentrations.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Seino S. (1999) ATP-sensitive potassium channels: A model of heteromultimeric potassium channel/ receptor assemblies. *Annu Rev Physiol* 61, 337-62.
2. Hokoshiki H, Sunagawa M, Seki T, Sperlakis N. (1998) ATP-sensitive $K^+$ channels in pancreatic, cardiac and vascular smooth muscle cells. *Am. J. Physiol.* 274:C25-C37.
3. Aguilar-Bryan L, C G Nichols, H Herrera-Sosa, K Nguy, J Bryan, D A Nelson. (1995) Cloning of the high affinity SUR: a regulator of insulin secretion. *Science* 268, 423-426.
4. Inagaki N, T Gonoi, J P Clement IV, C Z Wang, L Aguilar-Bryan, J Bryan, S Seino. (1996) A family of SURs determine the pharmacological properties of ATP-sensitive $K^+$ channels. *Neuron* 16, 1011-1017.
5. Chutkow W A, Simon M C, Le Beau M M, Burant C F (1996) Cloning, tissue expression and chromosomal localization of SUR2, the putative drug-binding subunit of cardiac, skeletal muscle and vascular $K_{ATP}$ channels. *Diabetes* 45:1439-1445.
6. Inagaki N, Tsuura Y, Namba N, Masuda K, Gonoi T, Horie M, Seino Y, Mizuta M, Seino S (1995) Cloning and functional characterisation of a novel ATP-sensitive potassium channel ubiquitously expressed in rat tissues, including pancreatic islets, pituitary, skeletal muscle and heart. *J Biol Chem* 271:24321-24324.
7. Isomoto S, Kondo C, Yamada M, Matsumoto S, Higashiguchi O, et al. (1996) A novel sulfonylurea receptor forms with BIR (Kir.6.2) a smooth muscle type ATP-sensitive $K^+$ channel. *J Biol Chem* 271, 24321-24.
8. Inagaki N, T Gonoi, J P Clement IV, N Namba, J Inazawa, G Gonzalex, L Aguilar-Bryan, S Seino, J Bryan. (1995) Reconstitution of $IK_{ATP}$: an inward rectifier subunit plus the SUR. *Science* 270, 1166-1170.
9. Sudhof T C (1995) The synaptic vesicle cycle: a cascade of protein-protein interactions. *Nature* 375, 645-653.
10. Weber, T. Zemelman B V, McNew J A, Westermann B, Gmachi M, Parlati F, Soliner T H, Rothman J E. (1998) SNAREpins: minimal machinery for membrane fusion. *Cell* 92, 759-772.
11. Ashcroft F M and S J H Ashcroft. (1992) Mechanisms of insulin secretion. In Insulin: Molecular Biology to Pathology. Ashcroft F M, Ashcroft S J H, Eds. Oxford, UK, Oxford University Press, p. 93-150.
12. Rajan A S, L Aguilar-Bryan, D A Nelson, G C Yaney, W H Hsu, D L Kunze, E Boyd. (1990) Ion channels and insulin secretion. *Diabetes Care* 13, 340-363.
13. Lawson K. (2000) Potassium channel openers as potential therapeutic weapons in ion channel disease. *Kidney International* 57:838-845.
14. Shyng S-L, Nichols C G. (1997) Octameric stoichiometry of the $K_{ATP}$ channel complex. *J. Gen. Physiol.* 110, 655.
15. Thomas P M, G J Cote, N Wohlik, B Haddad, P M Mathew, W Rabl, L Aguilar-Bryan, R F Gagel, J Bryan. (1996) Mutations of SUR gene in familial hyperinsulinemic hypoglycemia of infancy. *Science* 268, 423-426.
16. Tucker S J, Gribble F M, Zhao C, Trapp S, Aschroft F M. (1997) Truncation of Kir6.2 produces ATP-sensitive $K^+$ channels in the absence of the sulphonylurea receptor. *Nature* 387,179-83.
17. Tucker S J, Gribble F M Poks, P, Trapp S, Ryder T J, et al. (1998) Molecular determinants of $K_{ATP}$ channel inhibition by ATP. *EMBO J.* 17:3290-96.
18. Gribble F M, Tucker S J, Ashcroft F M. (1997) The essential role of the Walker A motifs of SUR1 in $K_{ATP}$ channel activation by Mg-ADP and diazoxide. *EMBO J.* 16,1145-52.
19. Shyng S-L, Ferrigni T, Nichols C G. (1997) Regulation of $K_{ATP}$ channel activity by diazoxide and MgADP distinct functions of the two nucleotide binding folds of sulfonylurea receptor. *J. Gen. Physiol.* 110, 643-54.
20. Nichols C G, Shung S-L, Nestorowicz A, Glaser B, Clement C G IV, Gonzales G, Aguilar-Bryan L, Bryan J P. (1996) Adenosine diphosphate as an intracellular regulator of insulin secretion. *Science* 272, 1785-87.
21. Ueda K, Inagaki N, Seino S. (1997) Mg-ADP antagonism to $Mg^{2+}$-independent ATP binding of the sulfonylurea receptor SUR1. *J. Biol. Chem.* 272, 22983-86.
22. Babenko A P, Gonzales G, Bryan J. (1999) Two regions of sulfonylurea receptor specify the spontaneous bursting and ATP inhibition of $K_{ATP}$ chanel isoforms. *J Biol Chem* 274:11587-11592.
23. Hambrock A, Loffler-Walz C, Kloor D, Delabar U, Horio Y, Kurachi Y, Quast U (1999) ATP-sensitive $K^+$ channel modulator binding to sulfonylurea receptors SUR2A and SUR2B: Opposite effects of MgADP. *Mol Pharmacol* 55:832-840.
24. Schwanstecher M, Sieverding C, Dorschner H. Gross I, Aguilar-Bryan L, Schwanstecher C, Bryan J (1998) Potassium channel openers require ATP to bind to and act through sulfonylurea receptors. *EMBO J* 17:5529-5535.
25. Lawson K. (2000) Potassium channel openers as potential therapeutic weapons in ion channel disease. *Kidney International* 57:838-845.
26. Fasshauer D, Sutton R B, Brunger A T, Jahn R. (1998) Conserved structural features of the synaptic fusion complex: SNARE proteins reclassified as Q- and R-SNAREs. *Proc. Natl. Acad. Sci. USA* 95, 15781-15786.
27. Sutton R B, Fasshauer D, Jahn R, Brunger A T. (1998) Crystal structure of a SNARE complex involved in synaptic exocytosis at 2.4A resolution. *Nature* 395, 347-353.
28. Lin R C, Scheller R H. (1997) Structural organization of the synaptic exocytosis core complex. *Neuron* 19, 1087-1094.
29. Chen U A, Scales S J, Patel S M, Doung Y C, Scheller R H. (1999) SNARE complex formation is triggered by $Ca^{2+}$ and dives membrane fusion. Cell 97, 165-174.
30. Ungermann C, Sato K, Wickner W. (1998) Defining the functions of trans-SNARE pairs. *Nature* 396, 543-548.
31. Ausubel, F. M., et al., Current Protocols in Molecular Biology (John Wiley and Sons, Inc., Media, Pa.).
32. Brent, R. et al., (1985) *Cell* 43, 729-736.
33. Fields, S. et al. (1989) *Nature* 340, 245.
34. Chien, C.-t. et al. (1991) *Proc. Natl. Acad. Sci. U.S.A.* 88, 9578.
35. Durfee, T. et al. (1993) *Genes & Development* 7, 555.
36. Bartel, P. et al. (1993) *BioTechniques* 14, 920-924.
37. Yang, X. et al. (1992) *Science* 257, 680.
38. Gyuris, J. et al. (1993) *Cell* 75, 791-803.
39. Calabrese, G S. et al. Anal. Chem. 59:833-837 (1987).
40. Ngeh-Ngwainbi, J. et al. (1990) *Biosens. Bioelectronics* 5, 13-26.
41. Rajakovic, L. et al. (1989) *Anal. Chim. Acta* 217, f11-121.
42. Roederer, J. E., and Bastiaans, G. J. (1983) *Anal. Chem.* 55, 2333-2336.
43. Ward, M. D., and Buttry, D. A. (1990) *Science* 249, 1000-1007.
44. Ngo, T T., Ed. in ELECTROCHEMICAL SENSORS IN IMMUNOLOGICAL ANALYSIS (Plenum Press, New York, N.Y.) (1987).
45. Corsel, J. W. et al., (1986) *J. Colloid. Interface Sci.* 111, 544-554.
46. Jonsson, U. et al. (1985) *Colloids Surfaces* 13, 333-339.
47. Vroman, L., and Adams, A. L. (1969) *Surface Sci.* 16, 438-446.
48. Nellen, Ph. M., and Lukosz, W. (1990) *Sensors Actuators* B1, 592-596.
49. Cullen, D. C., et al. (1988) *Biosensors* 3, 211-225.
50. Liedberg, B., et al. (1983) *Z. Phys.* 4, 299-304.

I claim:

1. A method of screening for compounds that affect the binding between 1) a full length syntaxin-1A protein or a fragment thereof which comprises the H3 domain of a syntaxin-1A protein and 2) a nucleotide binding fold-1 (NBF1) and/or nucleotide binding fold-2 (NBF2) protein wherein the NBF1 and/or NBF2 are derived from a sulfonylurea receptor (SUR) selected from the group consisting of SUR1, SUR2A, SUR2B and SUR2C comprising:

(a) contacting the syntaxin-1A protein or the fragment thereof and the NBF1 and/or NBF2 in the presence of a test compound;

(b) determining the effect of the test compound on the binding of the syntaxin-1 A protein or the fragment thereof and the NBF1 and/or NBF2, wherein the syntaxin-1A protein or fragment thereof is capable of binding to NBF1 and/or NBF2, and wherein a difference in the binding between the syntaxin-1A protein or fragment and the NBF1 and/or NBF2 in the presence of the test compound and the binding between the syntaxin-1A protein or fragment and the NBF1 and/or NBF2 in the absence of the test compound (control) indicates that the compound affects the binding between the syntaxin-1A protein or fragment and the NBF1 and/or NBF2.

2. The method according to claim 1, wherein the SUR is selected from the group consisting of SUR1 and SUR2A.

3. The method according to claim 1, wherein one of the syntaxin-1A protein or fragment thereof and the NBF1 and/or NBF2 is attached to a solid support.

4. The method according to claim 3, wherein the solid support is glutathione beads.

5. The method according to claim 3, wherein binding is measured using antibodies to one of the syntaxin-1A protein and the NBF1 and/or NBF2.

6. The method according to claim 1 wherein the syntaxin-1A comprises the sequence shown in SEQ ID NO:1.

7. The method according to claim 1 wherein the H3 domain comprises amino acid residues 191-266 shown in SEQ ID NO:1.

8. The method according to claim 1 wherein the NBF1 comprises the sequence shown in SEQ ID NO:2 or 4.

9. The method according to claim 8 wherein the NBF2 comprises the sequence shown in SEQ ID NO:3 or 5.

* * * * *